United States Patent [19]
Wilk

[11] Patent Number: 6,106,463
[45] Date of Patent: Aug. 22, 2000

[54] MEDICAL IMAGING DEVICE AND ASSOCIATED METHOD INCLUDING FLEXIBLE DISPLAY

[76] Inventor: Peter J. Wilk, 185 W. End Ave., New York, N.Y. 10023

[21] Appl. No.: 09/063,113

[22] Filed: Apr. 20, 1998

[51] Int. Cl.$^7$ .................................................. A61B 8/00
[52] U.S. Cl. ............................................................. 600/437
[58] Field of Search ................................ 600/437, 440, 600/443, 449; 73/625, 627; 345/22, 55; 367/153–155; 128/916

[56] References Cited

U.S. PATENT DOCUMENTS

| | | |
|---|---|---|
| 3,552,382 | 1/1971 | Mount . |
| 3,927,662 | 12/1975 | Ziedonis . |
| 4,048,616 | 9/1977 | Hart et al. . |
| 4,623,219 | 11/1986 | Trias . |
| 4,646,158 | 2/1987 | Ohno et al. . |
| 4,757,820 | 7/1988 | Itoh . |
| 5,091,893 | 2/1992 | Smith et al. . |
| 5,099,459 | 3/1992 | Smith . |
| 5,135,001 | 8/1992 | Sinofsky et al. . |
| 5,163,436 | 11/1992 | Saitoh et al. . |
| 5,167,231 | 12/1992 | Matsui . |
| 5,203,336 | 4/1993 | Iida et al. . |
| 5,394,877 | 3/1995 | Orr et al. . |
| 5,435,311 | 7/1995 | Umemura et al. . |
| 5,437,278 | 8/1995 | Wilk . |
| 5,488,952 | 2/1996 | Schoolman . |
| 5,611,343 | 3/1997 | Wilson . |
| 5,611,345 | 3/1997 | Hibbeln . |
| 5,619,999 | 4/1997 | Von Behren et al. . |

*Primary Examiner*—Marvin M. Lateef
*Assistant Examiner*—Alj M. Imam
*Attorney, Agent, or Firm*—R. Neil Sudol; Henry D. Coleman

[57] ABSTRACT

A medical imaging device includes one or more planar substrates, one or more flat video screens provided on the substrates, a flexible bag connected to the substrates, and a scanner operatively connected to the video screens for providing video signals thereto. The bag is disposed on a side of the substrates opposite the video screens and is filled with a fluidic medium capable of transmitting ultrasonic pressure waves. The video signals encodes images of internal tissues of a patient upon placement of the flexible bag with the medium, the substrates and the video screens against the patient.

31 Claims, 12 Drawing Sheets

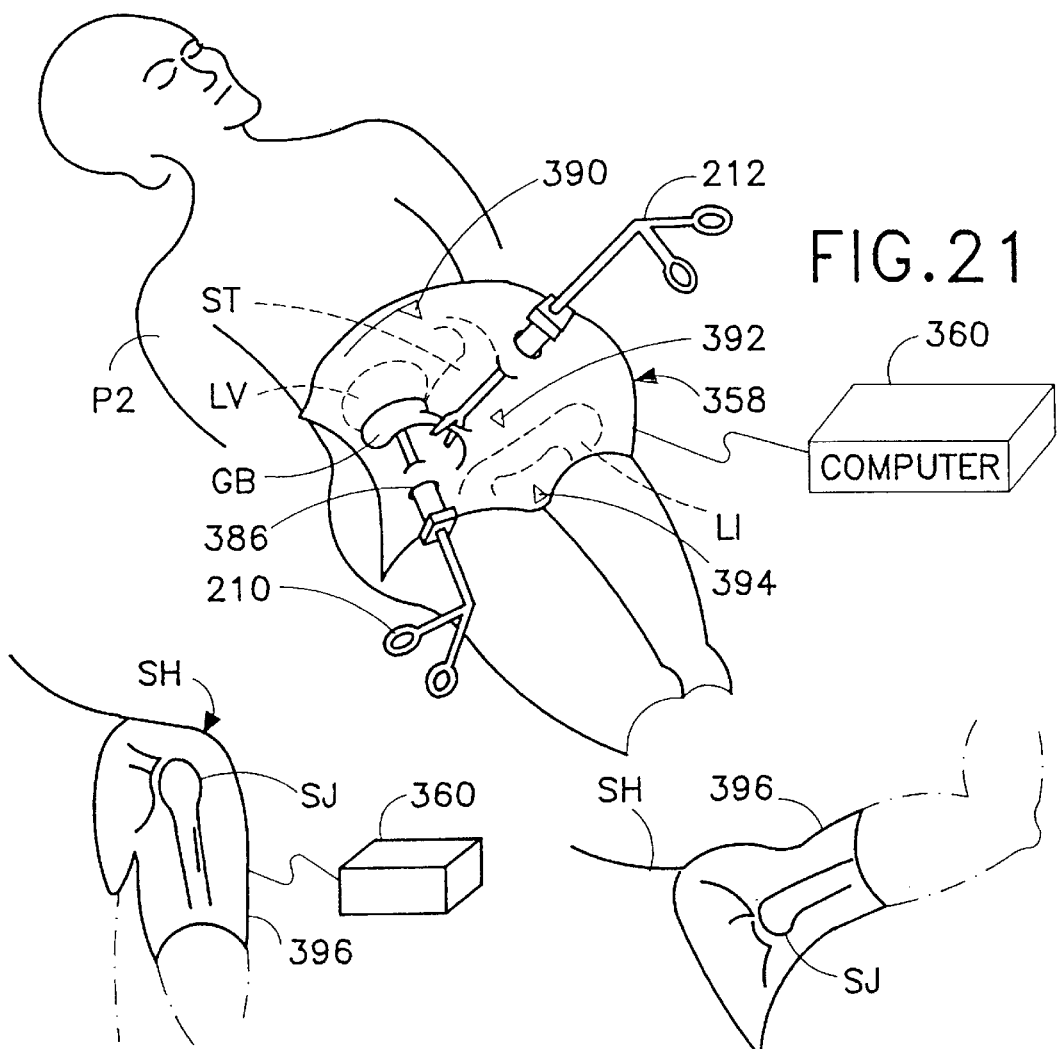
FIG.21
FIG.22A  FIG.22B
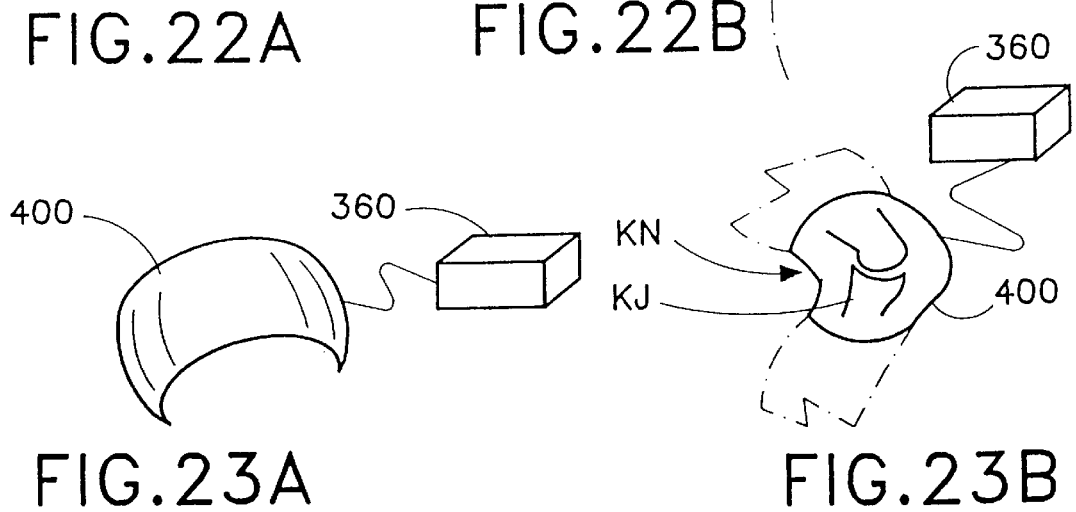
FIG.23A  FIG.23B

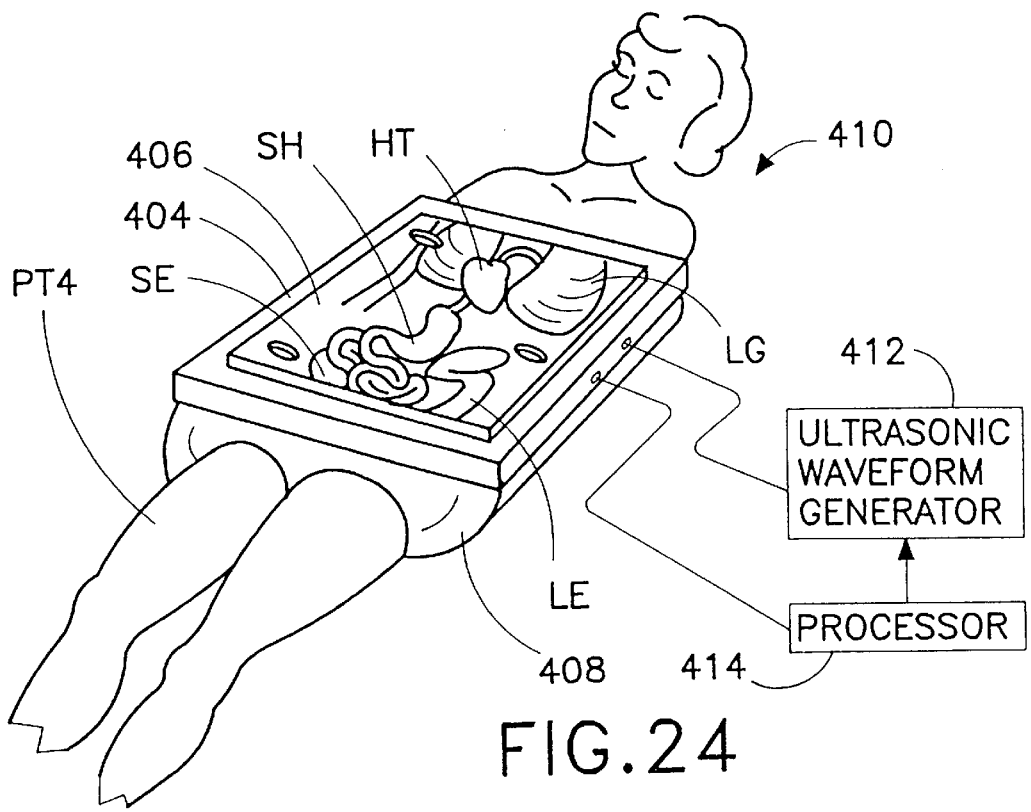
FIG.24
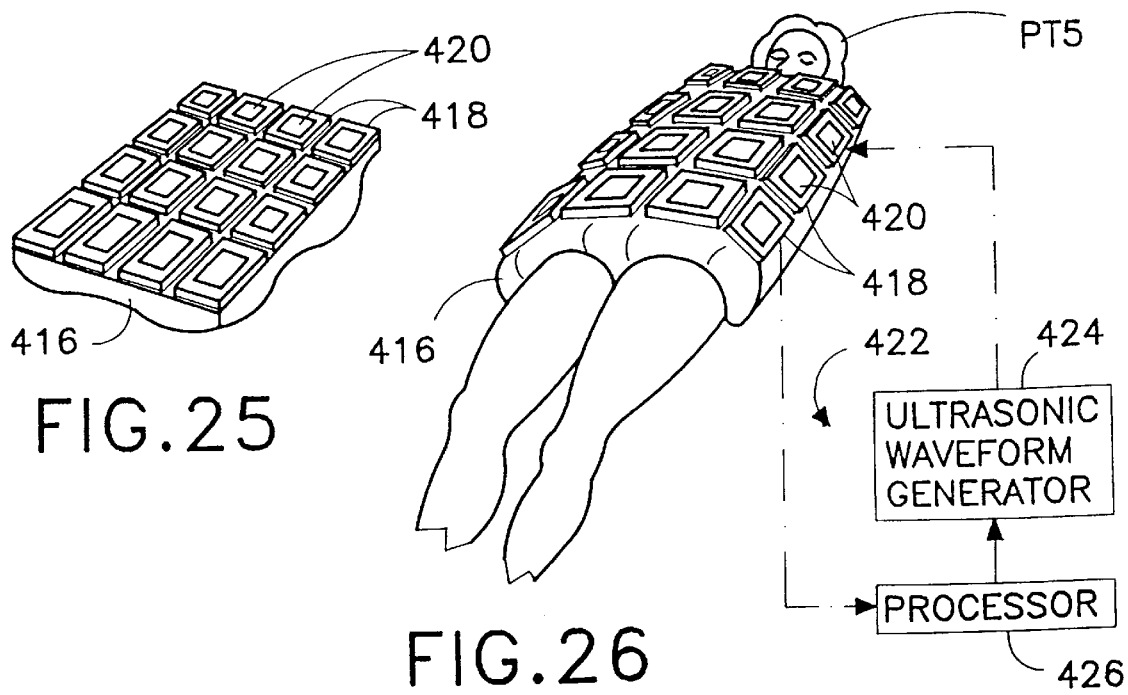
FIG.25
FIG.26

MEDICAL IMAGING DEVICE AND ASSOCIATED METHOD INCLUDING FLEXIBLE DISPLAY

BACKGROUND OF THE INVENTION

This invention relates to an imaging device or system. The imaging device or system is especially useful as a medical system. More particularly, this invention relates to a device or system which determines three-dimensional shapes of objects such as internal organs of a patient preferably by using ultrasonic pressure waves. This invention also relates to a method useful in medical operations.

In recent years, the escalation of medical costs has captured substantial media and regulatory attention. One reason for the escalating costs is the ever increasing use of expensive machines and testing techniques. Computed assisted tomography (CAT scanning), magnetic resonance imaging (MRI) and some radiological techniques have been in the forefront of contributing to mounting medical costs. In addition to being expensive, these devices are heavy and bulky, making them ill suited to transport.

In this age of rapidly escalating medical costs, minimally invasive operations have become the method of choice for diagnosis and treatment. In many cases, endoscopic, laparoscopic and radiographic techniques have superseded older diagnostic and therapeutic surgical techniques.

OBJECTS OF THE INVENTION

An object of the present invention is to provide an imaging device or system which is relatively inexpensive and easy to transport.

It is another object of the present invention to provide an alternative to conventional medical imaging systems.

A further object of the present invention is to provide a medical imaging system which exhibits reduced costs over conventional imaging systems such as CAT scanners and MRI machines.

A particular object of the present invention is to provide a medical imaging system which can be used during the performance of so-called minimally invasive medical operations.

It is an additional object of the present invention to provide a medical imaging system which is portable.

Another object of the present invention is to provide a medical operating method which provides real time imaging in a cost effective manner.

These and other objects of the present invention will be apparent from the drawings and descriptions herein.

SUMMARY OF THE INVENTION

A medical imaging device comprises, in accordance with an embodiment of the present invention, a planar substrate, a substantially flat video screen provided on the substrate, a flexible bag connected to the substrate, and a scanner operatively connected to the video screen for providing a video signal thereto. The bag is disposed on a side of the substrate opposite the video screen and is filled with a fluidic medium capable of transmitting ultrasonic pressure waves. The video signal encodes an image of internal tissues of a patient upon placement of the flexible bag with the medium, the substrate and the video screen against the patient.

An imaging device comprises, in accordance with another embodiment of the present invention, a plurality of substantially planar substrates, at least one flexible connection coupling the substrates to one another so that the substrates are extendable at a variable angle with respect to one another, a plurality of video screens each attached to one of the substrates, and a scanner operatively connected to the video screens for providing respective video signals thereto, the video signals each encoding an image of objects located near a respective one of the substrates.

It is contemplated that the scanner is an ultrasonic scanner and includes at least one electroacoustic transducer and at least one acoustoelectric transducer. Where a flexible bag filled with a fluidic medium is attached to the substrate or substrates, the transducers are both attached at least indirectly to the substrate(s) so that ultrasonic pressure waves can travel through the fluidic medium from the electroacoustic transducer and to the acoustoelectric transducer.

The scanner is preferably provided with an analyzing component, generally a specially programmed digital computer, for analyzing scanner sensor signals and determining therefrom three-dimensional shapes of objects being scanned.

The imaging device of the present invention is considered to be particularly advantageous in medical diagnosis and treatment procedures. The substrate or substrates with one or more video screens are disposed on a selected body portion of a patient, for example, the abdomen or a shoulder or knee, so that the substrate and the video screen overlie the selected body portion and so that the video screen or screens are facing away from the body portion. After the disposition of the substrate and the video screen, or the multiple substrates and the multiple video screens next to the patient, the scanner is operated to generate one or more video signals and transmit those signals to the video screens. The video signals encode images of internal tissues of the patient. Preferably, the video screens are operated to reproduce the images so that representations of internal tissues (e.g., organs) as displayed on the video screens substantially overlie respective corresponding actual tissues (organs) of the patient. Thus, for many purposes and applications, it appears to the user (generally a physician) that he or she is able to see through the skin and other overlying tissues to selected underlying tissues.

To enable or facilitate an alignment of the displayed tissue representations and the respective underlying actual tissues, it is recommended that markers be placed in prespecified locations on the patient. The markers are easily recognized by the analyzing computer and serve to define a reference frame whereby the position and the orientation of the multiple video screens relative to the patient's internal tissues are detectable. Accordingly, the position and the orientation of each video screen relative to the internal tissues and organs of the patient are determined to enable the display on the video screens of images of tissues underlying the different screens.

The imaging device or system is preferably provided with a number of ancillary components or functional subcomponents for facilitating use of the system as a medical diagnostic and therapeutic tool. For example, the analyzing component may include a module, typically realized as a programmed general computer circuit, for highlighting a selected feature of the internal organs of the patient. The highlighting may be implemented by changing the color or intensity of the selected feature relative to the other features in the displayed image, thus providing a visual contrast of the selected feature with respect to the other features of the displayed image. An intensity change may be effectuated by essentially blacking or whiting out the other portions of the image so that the selected feature is the only object displayed on the video screen.

Another ancillary component for enhancing the usefulness of the imaging device or system is voice-recognition circuitry operatively connected to the analyzing computer. Voice recognition circuity is especially beneficial for medical applications in that doctors must frequently have their hands (and even feet) available for operating medical equipment. In conventional medical procedures, voice control is exerted via attendant personnel: the assistants are requested by the lead physician to perform desired tasks. The voice recognition circuitry of the present invention is used, for instance, to request highlighting of a selected organ or removal of an organ from the image on the video screen. The removal of selected organs or tissues enables the user to view underlying organs. Viewing of the patient's internal structures may thus proceed in an ever more deeply penetrating sequence, with successive removal of different layers of tissues.

Yet another ancillary component is speech synthesis circuitry operatively connected to the analyzing computer. The voice recognition and speech synthesis circuitry together enable the user to interface with the imaging device as if the device were an operating room assistant. These ancillary components also free the physician's eyes to look at the flexible video screen.

The analyzing computer's tasks may extend well beyond normal image analysis and construction. The computer may be programmed for automated diagnosis based on pattern recognition. For example, the computer may be programmed to recognize a bloated appendix by comparing the image data with prestored data identifying normal and inflamed appendices. The computed diagnosis may be communicated to the physician via the speech synthesis circuitry: "Enlarged appendix—possible appendicitis—recommend immediate removal."

Where the imaging device comprises multiple video screens, the device is advantageously provided with a plurality of apertures, for example, in the interstitial spaces between the video screens, enabling traversal of the device by medical instruments. The distal ends of the medical instruments, inserted into the patient in the field of view of the imaging system, are displayed on the video screens together with internal target tissues of the patient. In this way, laparoscopic surgery as well as other invasive operations, whether diagnostic or therapeutic, may be performed with the aid of real-time visual images of the patient's internal tissues displayed on the video screens. Laparoscopic surgery is simplified by eliminating the need for a laparoscope. Laparoscope elimination enables a reduction in the number of perforations made in the patient or, alternatively, enables the insertion of another laparoscopic instrument with the same number of perforations. Other operations implemented by inserting instruments through the flexible video screen include liver biopsies, kidney biopsies, and pleural biopsies and the placement of tubular members, including drains and catheters, for such techniques as thoracentesis and abscess drainage.

An additional ancillary component for enhancing the usefulness of the imaging device or system in accordance with the present invention is a transceiver interface for operatively connecting the scanner, including the analyzing computer, to a long-distance telecommunications link. The image data is transmitted over the telecommunications link to a video monitor at a remote location, thereby enabling observation of the patient's internal tissues by specialists in distant cities. These specialists may provide diagnostic and treatment advice to people at the location of the patient. Also, a surgical procedure may be exerted robotically under the control of the distant experts, as disclosed in U.S. Pat. Nos. 5,217,003 and 5,217,453 to Wilk.

The ultrasonic scanner utilizes ultrasonic pressure waves to collect the three-dimensional structural data from which the tissues images are derived or constructed. The ultrasonic scanner includes at least one electroacoustic transducer, an a-c current generator operatively connected to the transducer for energizing the transducer with an electrical signal of a pre-established ultrasonic frequency to produce a first pressure wave, and at least one acoustoelectric transducer. The analyzing computer is operatively connected to the acoustoelectric transducer for determining three-dimensional shapes of the objects by analyzing signals generated by the acoustoelectric transducer in response to second pressure waves produced at the objects in response to the first pressure wave.

In a particular embodiment of the invention, at least one of the ultrasonic transducers is mounted to the substrate or to one of the substrates. Typically, the electroacoustic transducer is one of a plurality of electroacoustic transducers and the acoustoelectric transducer is one of a plurality of acoustoelectric transducers, all mounted to the substrate or substrates. This configuration is especially portable: it is compact and lightweight.

In accordance with another feature of the present invention, the ultrasonic pressure waves are produced in different frequency ranges. The different frequencies penetrate to different depths. Thus, the multiple frequencies provide different kinds of structural data to the analyzing computer. Where the ultrasonic scanner includes multiple electroacoustic transducers, each such transducer may be capable of generating pressure waves in multiple frequency ranges. Alternatively, the electroacoustic transducers may be dedicated to generating ultrasonic pressure waves in respective frequency ranges different from the frequency ranges of the other electroacoustic transducers. In that case, the a-c current generator is operatively connected to the electroacoustic transducers for energizing the electroacoustic transducers with electrical signals of different pre-established ultrasonic frequencies. Similarly, the imaging device may include multiple acoustoelectric transducers each capable of sensing a pressure wave in a respective frequency range different from the frequency ranges of the other of the acoustoelectric transducers.

Where the imaging device is used to diagnose or treat a limb or a joint, the planar substrates and the video screens attached thereto have sizes and possibly shapes which facilitate substantial conformity with the limb or joint.

To facilitate the use of the imaging device in invasive surgical procedures, the image provided on the video screen may be stereoscopic or holographic. Thus, manipulation of a medical instrument so that its distal end engages desired internal tissues is facilitated. The imaging device thus may include elements for providing a stereoscopic or holographic image to a viewer, the scanner including means for energizing the elements to produce the stereoscopic or holographic image.

A medical method in accordance with the present invention utilizes an imaging device including a plurality of planar substrates fastened to one another by flexible connectors, each of the substrates carrying a respective video screen, a scanner being operatively connected to the video screens. Pursuant to the method, the substrates with the video screens are disposed on a body portion of a patient so that the substrates and the video screens substantially conform to the body portion of the patient and so that the video screens are facing away from the body portion of the patient. After the disposition of the substrates and the video screens on the body portion of the patient, the scanner is operated to provide video signals to the video screens, the video signals encoding images of internal tissues of the patient.

Preferably, the video screens are operated to reproduce the images so that internal tissue representations as displayed on the video screens substantially overlie respective corresponding actual tissues of the patient.

The method also contemplates the placing of markers on the patient for facilitating the reproducing of the images so that the internal tissue representations on the video screens substantially overlie respective corresponding actual tissues of the patient.

The scanner is operated to provide the video images includes automatically analyzing scanner sensor signals and determining therefrom three-dimensional shapes of the internal tissues of the patient. An advantageous feature of the invention is highlighting a selected feature of the internal tissues of the patient on the video screens.

Where the imaging device is provided with a plurality of apertures, the method further comprises the step of inserting a distal end portion of a medical instrument into the patient through one of the apertures, and thereafter manipulating the instrument from outside the patient to perform an operation on at least one of the internal tissues of the patient, the images being viewed on the video screens while the instrument is being manipulated.

Where the scanner includes at least one electroacoustic transducer, an a-c current generator operatively connected to the transducer, at least one acoustoelectric transducer and an analyzing component operatively connected to the acoustoelectric transducer, the disposing of the substrates with the video screens on the body portion of the patient includes the step pf placing the substrates in pressure-wave-transmitting contact with the body portion of the patient. The operating of the scanner includes the steps of (1) transmitting a first electrical signal of a pre-established ultrasonic frequency from the current generator to the electroacoustic transducer for energizing the electroacoustic transducer to produce a first pressure wave, (2) transmitting the first pressure wave into the body portion of the patient, (3) transmitting, from the acoustoelectric transducer to the analyzing component, a second electrical signal corresponding to a second pressure wave produced at the internal tissues of the patient in response to the first pressure wave, and (4) operating the analyzing component to determine three-dimensional shapes of the internal tissues of the patient by analyzing the second electrical signal.

BRIEF DESCRIPTION OF THE DRAWINGS

FIG. 21 is a schematic perspective view showing use of the system of FIG. 20 in performing a laparoscopic operation.

FIGS. 22A and 22B are schematic perspective views showing use of another ultrasonographic device related to the present invention.

FIG. 23A is a schematic perspective view of a further ultrasonographic device related to the present invention.

FIG. 23B is a schematic perspective view showing use of the ultrasonographic device of FIG. 23A.

FIG. 24 is a schematic perspective view of an ultrasonographic device in accordance with the present invention.

FIG. 25 is a schematic perspective view of another ultrasonographic device in accordance with the present invention.

FIG. 26 is a schematic perspective view of the ultrasonographic device of FIG. 25, showing the device in use on a patient.

DESCRIPTION OF THE PREFERRED EMBODIMENTS

The present invention is directed chiefly to an imaging device and particularly to an ultrasonographic imaging device utilizable in diagnostic and therapeutic procedures. The ultrasonographic imaging device of the present invention is described generally hereinafter with reference to FIGS. 8 et seq. and particularly with reference to FIGS. 20 et seq. The ultrasonographic imaging device, and particularly image derivation or construction portions thereof, can be employed as an image generating apparatus or scanner 42 in the medical diagnostic system of FIG. 1 or a diagnostic image generating apparatus 78a, 78b, 78i in the medical diagnostic system of FIG. 4. Alternatively or additionally, the ultrasonographic imaging device can be employed in carrying out certain minimally invasive diagnostic or therapeutic operations, examples of which are illustrated schematically in FIGS. 12 and 13.

Figure 1:
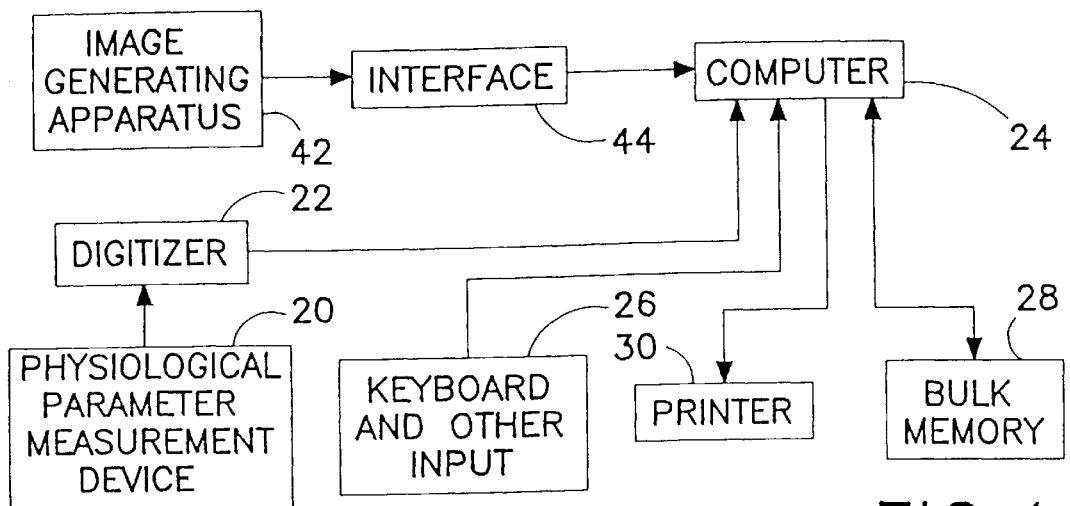
FIG. 1 is a block diagram of a medical diagnostic system, which may utilize or incorporate an ultrasonographic imaging device in accordance with the present invention.

As illustrated in FIG. 1, a medical diagnostic system comprises a device 20 for monitoring and measuring a biological or physiological parameter. Monitoring and measuring device 20 is juxtaposable to a patient for collecting individualized medical data about the patient's condition. Device 20 may take the form of an electronic thermometer, an electronic blood pressure gauge, a pulmonary function apparatus, a Doppler study apparatus, an EEG machine, an EKG machine, an EMG machine, or a pressure measurement device, etc., or include a plurality of such components.

Monitoring and measuring device 20 is connected at an output to a digitizer 22 which converts normally analog type signals into coded binary pulses and transmits the resulting digital measurement signal to a computer 24. Digitizer 22 may be incorporated into a housing (not shown) enclosing all or part of the monitoring and measuring device 20. Moreover, digitizer may be an integral part of monitoring and measuring device 20.

Computer 24 receives instructions and additional input from a keyboard 26. Keyboard 26 is used to feed computer 24 information for identifying the patient, for example, the patient's age, sex, weight, and known medical history and conditions. Such medical conditions may include past diseases and genetic predispositions.

Computer 24 is also connected to an external memory 28 and an output device 30 such as a printer or monitor. Memory 28 stores medical data for a multiplicity of previously diagnosed medical conditions which are detectable by analysis of data provided by monitoring and measuring device 20.

Figure 2:
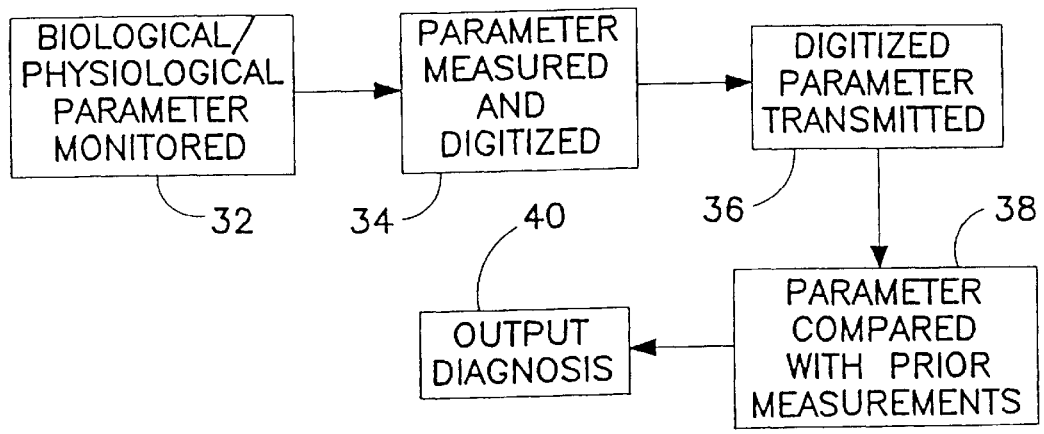
FIG. 2 is a flow-chart diagram illustrating steps in a mode of operation of the diagnostic system of FIG. 1.

As illustrated in FIG. 2, monitoring and measuring device 20 detects a magnitude of a predetermined biological or physiological parameter in a step 32. Digitizer 22 converts the detected magnitude into a pre-established digital format in a step 34 and transmits the digital signal to computer 24 in a step 36. Computer 24 is operated in a step 38 to compare the digitized data from monitoring and measuring device 20 with the data stored in memory 28 and to derive a diagnosis as to the patient's condition. The diagnosis is then communicated to the user (operator) and to the patient via output device 30 in a step 40.

If monitoring and measuring device 20 measures a physiological function characterized by a plurality of different variables, for example, the electric potential at different points on the patient's body (EEG, EKG, EMG), these variables may be broken down by computer 24 into one or more parameters, e.g., a frequency packet. The measured values of the pre-established parameters are then compared with parameter ranges stored in memory 28 for the type of parameter and the kind of patient, as characterized by sex, age, weight, etc. If the measured values of the pre-established parameters fall within expected ranges, as stored in memory 28, then computer 28 communicates a "normalcy" finding via printer 30. If, on the contrary, the measured values of one or more parameters fall outside the normal ranges, then a diagnosis of a possible medical condition is printed out.

As further illustrated in FIG. 1, the medical diagnostic system may comprise, in addition to or alternatively to monitoring and measuring device 20, image generating apparatus or scanner 42 for generating in electrically encoded form a visually readable image of an organic part of the patient. Scanner 42 may take the form of an MRI apparatus, a CAT scanner, an X-ray machine, an ultrasonography apparatus (see FIGS. 8–15 and 20), or a video camera with or without magnification optics for magnifying a sample on a slide. The video camera can be used for obtaining an image of a portion of a patient's skin.

Scanner 42 is connected via an interface 44 to computer 24.

Figure 3:
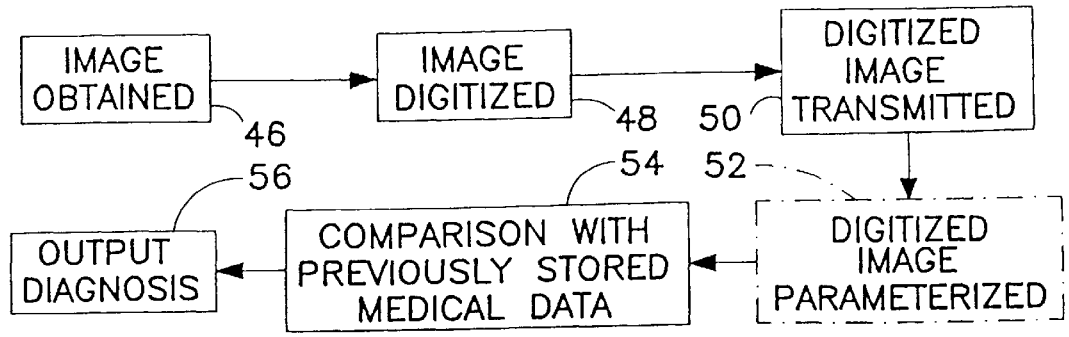
FIG. 3 is a flow-chart diagram illustrating steps in another mode of operation of the diagnostic system of FIG. 1.

As shown in FIG. 3, scanner 42 obtains an image of a tissue or organ in a step 46. The image is digitized, either by scanner 42 or interface 44 in a step 48, and is transmitted to computer 24 in a step 50. Computer 24 is operated in a step 52 to analyze the image from scanner 42 and determine specific values for a multiplicity of predetermined parameters. For example, in the event that scanner 42 takes the particular form of a video camera for dermatological diagnosis, an image of a skin surface of a patient is analyzed by computer 24 to derive such parameters as percentage of skin covered by abnormal condition, the range of sizes of individual ulcers, the range of color variation (e.g., whether bleeding is symptomatic).

The specific values of pre-established parameters calculated by computer 24 from electrically encoded images transmitted from scanner 42 are compared by computer 24 with previously determined parameter ranges stored in memory 28. For example, if a pregnant woman's fetus is being scanned by ultrasonography, the lengths of the fetal appendages, arms, legs, fingers, etc., are compared with each other and with respective fetal appendage ranges recorded in memory 28 for the stage of pregnancy, weight of the fetus, and possibly weight of the mother. In the event that any appendages are missing or are of abnormal length, a diagnosis as to possible deformity is printed out. Organs internal to the fetus may be similarly examined automatically by scanner 42 and computer 24. In more advanced stages of pregnancy, physiological functions such as the heart rate of the fetus may be automatically monitored for abnormal conditions.

The analysis performed by computer 24 on the image from scanner 42 will depend in part on the region of the patient's body being scanned. If a woman's breast or a person's cortex is being monitored for tumorous growths, computer 24 is programmed to separate the tissue image into regions of different textures. The different textured regions are parameterized as to size, shape and location and the derived parameters are compared to values in memory 30 to determine the presence of a tumor. Additional analysis is undertaken to detect lines in an image which may indicate the presence of an organic body.

A similar analysis is undertaken to evaluate a tissue specimen on a slide. The texture and line scanning may be repeated at different magnification levels if, for example, the tissue sample is a slice of an organ wall. On a high magnification level, the texture and line analysis can serve to detect microorganisms in blood.

Memory 28 may store entire images related to different diseases. For example, memory may store images of skin conditions in the event that scanner 42 takes the form of a video camera at a dermatological diagnosis and treatment facility. In a step 54 (FIG. 3), computer 24 compares the image of a patient's skin with previously stored images in memory 28, for example, by breaking down the current image into sections and overlaying the sections with sections of the stored images, at variable magnification levels.

In the event that scanner 42 takes the form of an MRI apparatus, a CAT scanner or an ultrasonographic scanner such as those described hereinafter with references to FIGS. 8–15 and 20, the images stored in memory 28 are of internal organic structures. In step 54 (FIG. 3), computer 24 compares images of a person's internal organs with previously stored organ images in memory 28. Computer 24 partitions the image from the MRI apparatus or CAT scanner into subareas and overlays the subareas with sections of the stored images, at variable magnification levels.

In a final step 40 (FIG. 3), computer 24 communicates the results of its diagnostic evaluation to a user or patient.

Figure 4:
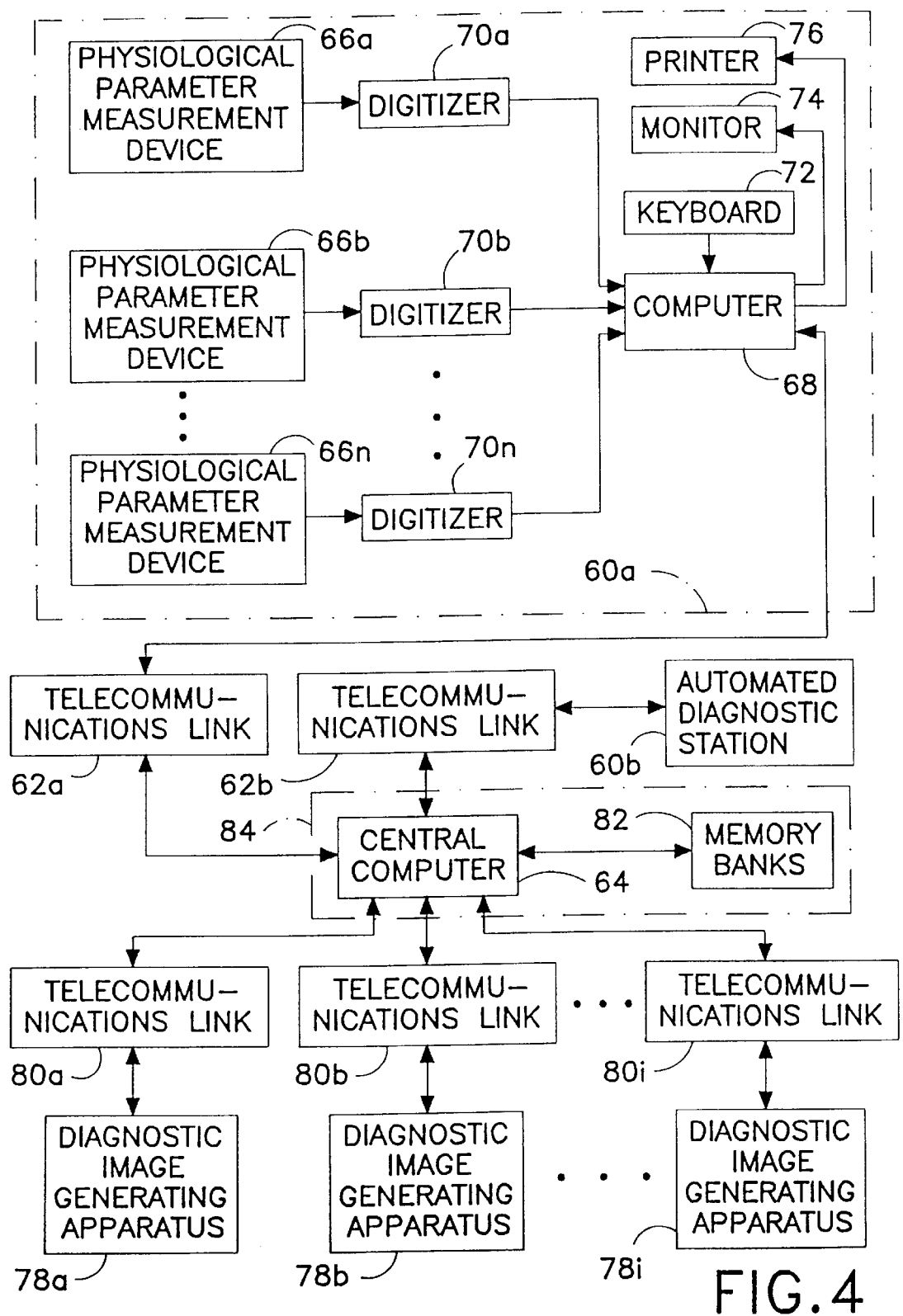
FIG. 4 a block diagram of a further medical diagnostic system.

As illustrated in FIG. 4, a medical diagnostic system comprises a plurality of remote automated diagnostic stations 60a and 60b connected via respective telecommunications links 62a and 62b to a central computer 64. Each diagnostic station 60a, 60b may take the form shown in FIG. 1, local computer 24 communicating via link 62a, 62b with central computer 64. Alternatively, each diagnostic station 60a, 60b may take the form shown in FIG. 4 and include a respective plurality of monitoring and measuring devices 66a, 66b, . . . 66n operatively connected to a local computer 68 via respective digitizer output units 70a, 70b, . . . 70n. Computer 68 is fed instructions and data from a keyboard 72 and communicates diagnostic results via a monitor 74 or printer 76. As discussed hereinabove with reference to monitoring and measuring device 20 of FIG. 1, each monitoring and measuring device 66a, 66b, . . . 66n is juxtaposable to a patient for collecting individualized medical data about the patient's condition. Monitoring and measuring devices 66a, 66b, . . . 66n may respectively take the form of an electronic thermometer, an electronic blood pressure gauge, a pulmonary function apparatus, a Doppler study apparatus, an EEG machine, an EKG machine, an EMG machine, or a pressure measurement device, etc.

Digitizers 70a, 70b, . . . 70n convert normally analog type signals into coded binary pulses and transmit the resulting digital measurement signals to computer 68. Digitizers 70a, 70b, . . . 70n may be incorporated into the housings or casing (not shown) enclosing all or part of the respective monitoring and measuring devices 66a, 66b, . . . 66n.

Keyboard 72 is used to feed computer 68 information for identifying the patient, for example, the patient's age, sex, weight, and known medical history and conditions. Such medical conditions may include past diseases and genetic predispositions.

As further illustrated in FIG. 4, a plurality of diagnostic image generating apparatuses or scanners 78a, 78b, . . . 78i are also connected to central computer 64 via respective hard-wired or wireless telecommunications links 80a, 80b, . . . 80i. Scanners 78a, 78b, . . . 78i each generate in electrically encoded form a visually readable image of an organic part of the patient. Scanners 78a, 78b, . . . 78i may each take the form of an MRI apparatus, a CAT scanner, an X-ray machine, an ultrasonography apparatus (FIGS. 8–15 and 20), or a video camera with or without magnification optics for magnifying a sample on a slide.

Because of the enormous quantity of data necessary for storing images, central computer 64 is connected to a bank of memories 82 at a central storage and information processing facility 84. Diagnosis of patient conditions may be undertaken by central computer 64 alone or in cooperation with local computers 24 or 68.

Figure 5:
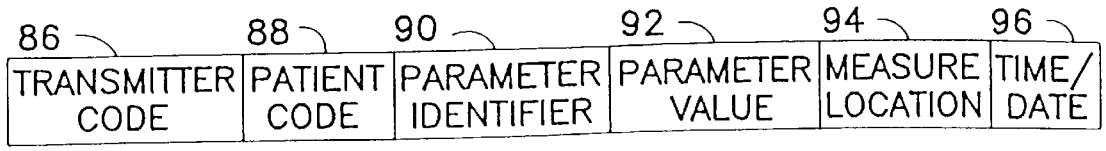
FIG. 5 is a diagram showing the composition of a data string or module used in the system of FIG. 4.

As illustrated in FIG. 5, local computers 24 and 68 transmit information to central computer 64 in data packets or modules each include a first string of binary bits 86 representing the transmitting station 60a, 60b, a second bit string 88 identifying the patient, a bit group 90 designating the parameter which is being transmitted, another bit group 92 coding the particular measured value of the parameter, a set of bits 94 identifying the point on the patient at which the measurement was taken, and another bit set 96 carrying the time and date of the measurement. Other bit codes may be added as needed.

Figure 6:
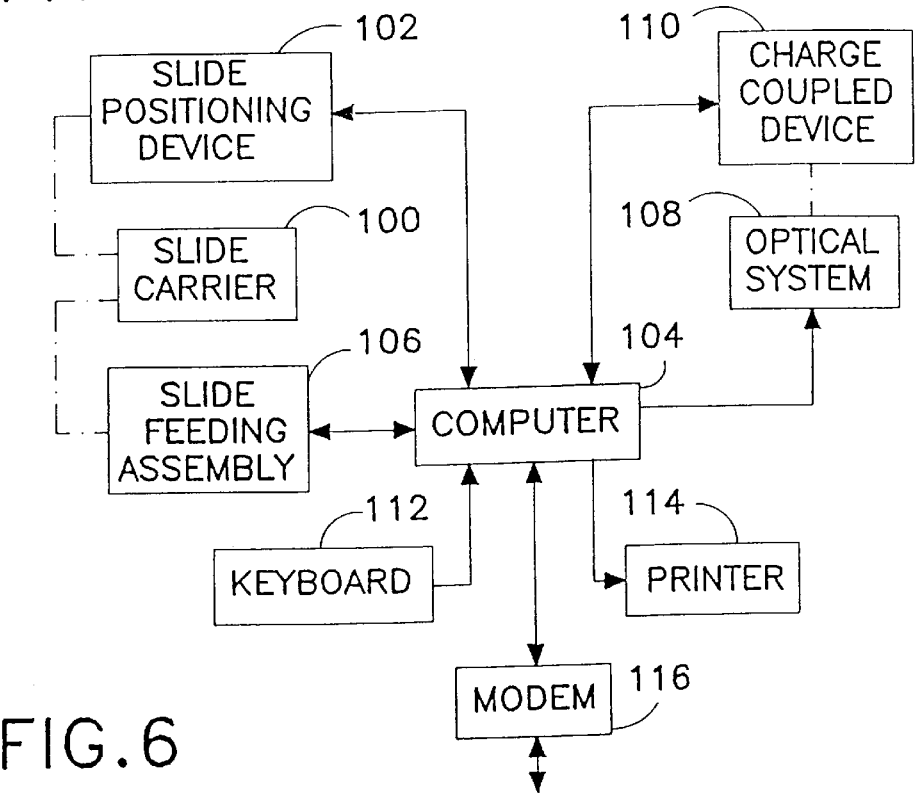
FIG. 6 is a block diagram of a computerized slide scanning system.

As shown in FIG. 6, a computerized slide scanning system comprises a slide carrier 100 mountable to a microscope stage and a slide positioning device 102 mechanically linked to the slide carrier 100 for shifting the carrier along a path determined by a computer 104. Computer 104 may be connected to an optional transport or feed assembly 106 which delivers a series of slides (not shown) successively to slide carrier 100 and removes the slides after scanning.

Computer 104 is also connected to an optical system 108 for modifying the magnification power thereof between successive slide scanning phases. Light emerging from optical system 108 is focused thereby onto a charge coupled device ("CCD") 110 connected to computer 104 for feeding digitized video images thereto.

Computer 104 performs a line and texture analysis on the digitized image information from CCD 110 to determine the presence of different organic structures and microorganisms. The different textured regions are parameterized as to size, shape and location and the derived parameters are compared to values in a memory to identify microscopic structures. The texture and line scanning is repeated at different magnification levels.

Computer 104 may be connected to a keyboard 112, a printer 114, and a modem 16. Modem 116 forms part of a telecommunications link for connecting computer 104 to a remote data processing unit such as computer 64 in FIG. 4.

Image generating apparatus 42 in FIG. 1 may take the form of the computerized slide scanning system of FIG. 6.

Figure 7:
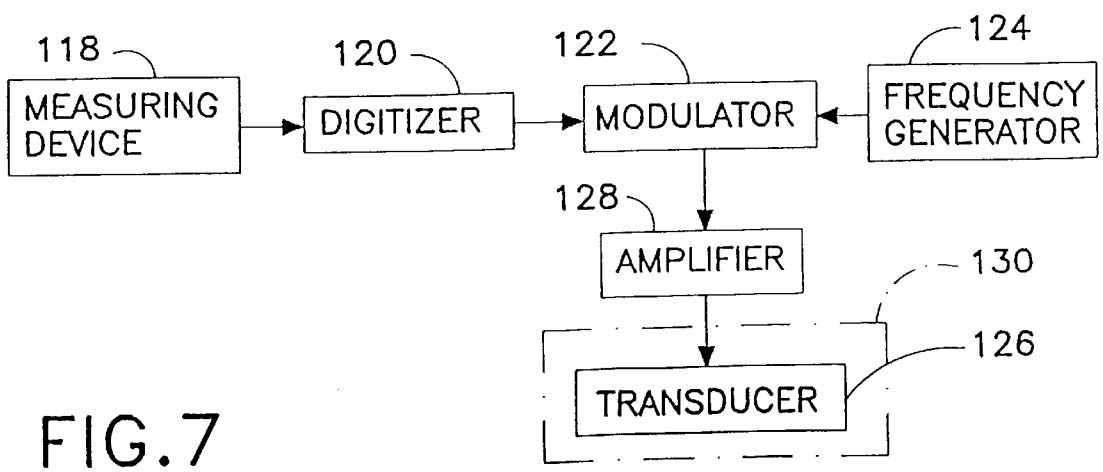
FIG. 7 is a block diagram of a device for measuring a diagnostic parameter and transmitting the measurement over the telephone lines.

As shown in FIG. 7, a device for measuring a diagnostic parameter and transmitting the measurement over the telephone lines comprises a monitoring and measuring device 118 which may take the form, for example, of an electronic thermometer, an electronic blood pressure gauge, a pulmonary function apparatus, a Doppler study apparatus, an EEG machine, an EKG machine, an EMG machine, or a pressure measurement device, etc., or include a plurality of such components. Monitoring and measuring device 118 is connected at an output to a digitizer 120 which in turn is coupled to a modulator 122. Modulator 122 modulates a carrier frequency from a frequency generator 124 with the data arriving from monitoring and measuring device 118 via digitizer 120 and transmits the modulated signal to an electroacoustic transducer 126 via an amplifier 128. Transducer 126 is removably attachable via a mounting element 130 to the mouthpiece of a telephone handset (not shown) and generates a pressure wave signal which is converted by a microphone in the handset mouthpiece back to an electrical signal for transmission over the telephone lines. Of course, transducer 126 may be omitted and modulator 122 connected directly to a telephone line.

The system of FIG. 7 enables the transmission of specialized medical data directly over the telephone lines to a central computer (e.g. computer 64 in FIG. 4) which utilizes the incoming data to perform a diagnostic evaluation on the patient.

Monitoring and measuring device 118 may include traditional medical instrumentation such as a stethoscope or modern devices such as a CCD.

Figure 8:
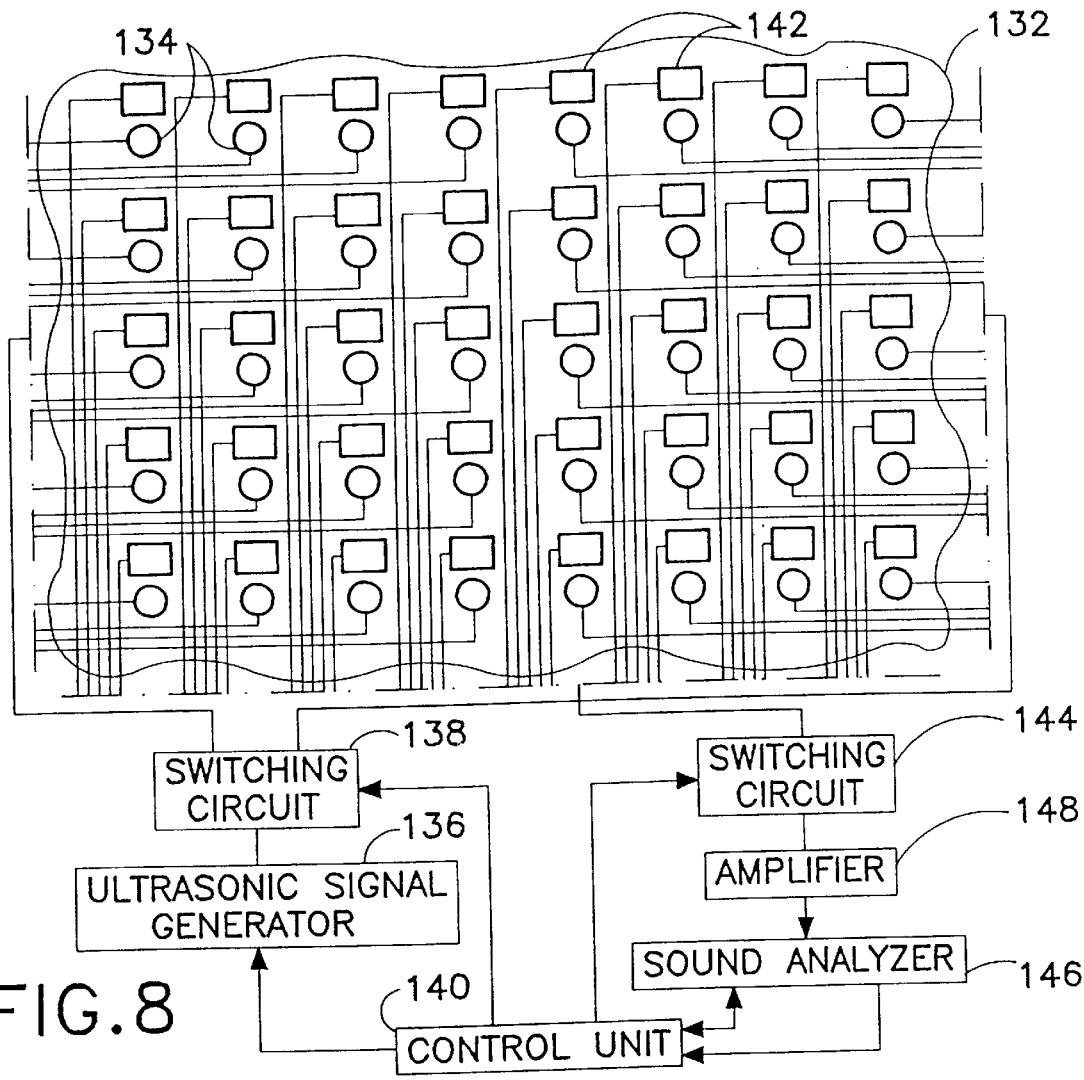
FIG. 8 is a diagram of an ultrasonography device.

FIG. 8 shows an ultrasonographic image generating apparatus which may be used in the medical diagnostic system of FIG. 1 (see reference designation 42) or in the medical diagnostic system of FIG. 4 (see reference designations 78a, 78b, . . . 78i). A flexible web 132 carries a plurality of piezoelectric electroacoustic transducers 134 in a substantially rectangular array. Transducers 134 are each connectable to an ultrasonic signal generator 136 via a switching circuit 138. Switching circuit 138 is operated by a control unit 140 to connect tranducers 134 to signal generator 136 in a predetermined sequence, depending on the area of a patient's body which is being ultrasonically scanned.

Web 132 also carries a multiplicity of acoustoelectric transducers or sensors 142 also arranged in a substantially rectangular array. Sensors 142 are connected to a switching circuit 144 also operated by control unit 140. An output of switching circuit 144 is connected to a sound or pressure wave analyzer 146 via an amplifier 148.

Web 132 is draped over or placed around a portion of a patient's body which is to be monitored ultrasonically. Control unit 140 then energizes signal generator 136 and operates switching circuit 138 to activate transducers 134 in a predetermined sequence. Depending on the transducer or combination of transducers 134 which are activated, control unit 140 operates switching circuit 144 to connect a predetermined sequence of sensors 142 to pressure wave analyzer 146. Pressure wave analyzer 146 and control unit 140 cofunction to determine three dimensional structural shapes from the echoes detected by sensors 142.

Control unit 140 is connected to ultrasonic signal generator 136 for varying the frequency of the generated signal.

Figure 9:
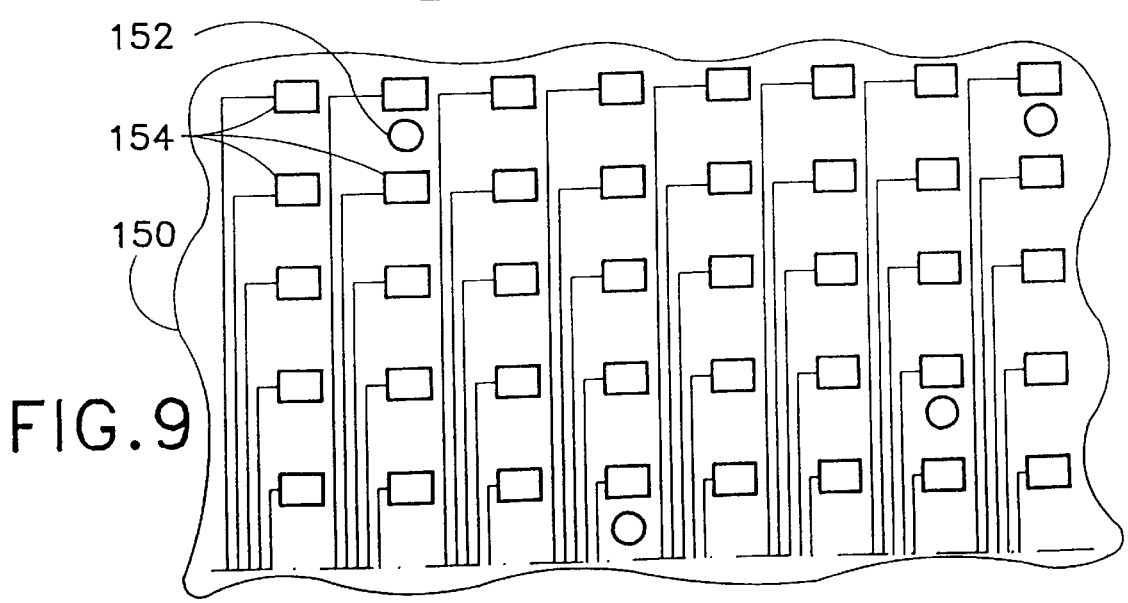
FIG. 9 is a diagram showing a modification of the device of FIG. 8.

FIG. 9 shows a modified ultrasonography web 150 having a limited number of electroacoustic transducers 152 and generally the same number and disposition of sensors 154 as in web 132.

Web 132 or 150 may be substantially smaller than illustrated and may correspondingly carry reduced numbers of transducers 134 and 152 and sensors 142 and 154. Specifically, web 132 or 150, instead of being a sheet large enough to wrap around a torso or arm of a patient, may take a strip-like form which is periodically moved during use to different, predetermined locations on the patient. Control unit 140 and pressure wave analyzer 146 are programmed to detect internal organic structures from the data obtained at the different locations that the web 132 or 150 is juxtaposed to the patient.

Figure 10:
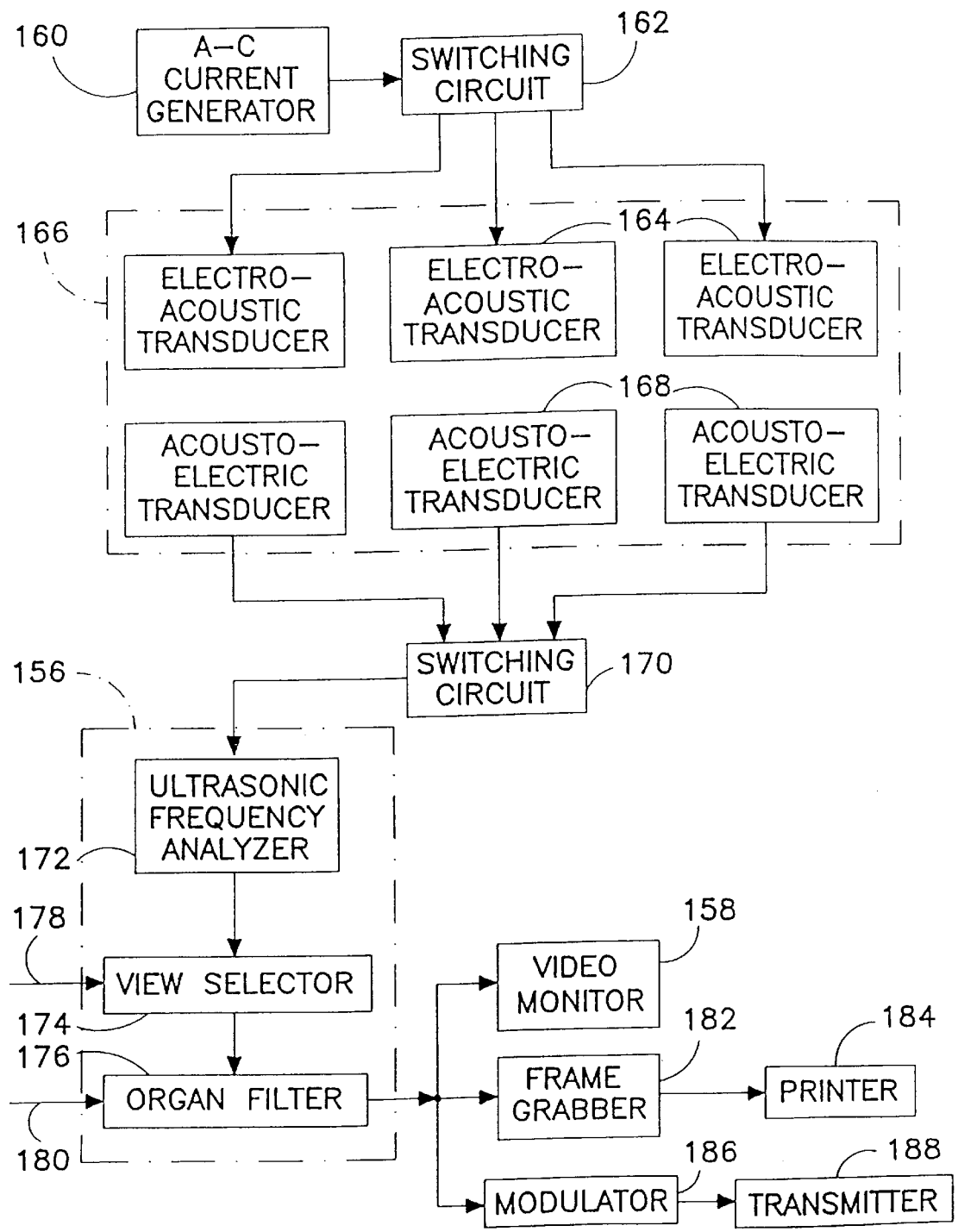
FIG. 10 is a block diagram of an ultrasonographic imaging apparatus similar to the device of FIGS. 8 and 9, for use in diagnostic and therapeutic procedures.

FIG. 10 illustrates a modification of the ultrasonography apparatus of FIGS. 8 and 9 which is employable in diagnostic or therapeutic operations involving the insertion of an instrument into a patient. A control unit 156 for performing operations of control unit 140 is connected at an output to a video monitor 158. As discussed hereinafter with reference to FIGS. 12 and 13, a diagnostician, surgeon or other medical specialist inserts a distal end of a medical instrument into a patient in response to video feedback provided by the ultrasonography apparatus including video monitor 158.

As further illustrated in FIG. 10, an a-c current or ultrasonic signal generator 160 is connected via a switching circuit 162 to different piezoelectric type electroacoustic transducers 164 in seriatum. Transducers 162 are mounted in interspaced fashion to a flexible web 166 which also carries an array of spaced piezoelectric type acoustoelectric transducers 168.

Web is placed adjacent to a skin surface of a patient. In some cases, it may be beneficial to provide a layer of fluid between the skin surface of the patient and the web 166 to facilitate ultrasonic wave transmission from web 166 to the patient and from the patient back to the web. In response to the periodic energization of transducers 162, ultrasonic pressure waves are reflected from internal organic structures of the patient and sensed by acoustoelectric transducers 168. Electrical signals generated by transducers 168 in response to the reflected pressure waves are fed via a switching circuit 170 to control unit 156.

As discussed hereinabove with reference to control unit 140 in FIG. 8, control unit 156 controls switching circuits 162 and 170 to energize emitting transducers 164 in a predetermined sequence and and to selectively couple receiving transducers 168 in a pre-established sequence to a pressure wave or ultrasonic frequency analyzer 172 in control unit 156. The sequencing depends on the portion of the patient being monitored.

In addition to pressure wave or ultrasonic frequency analyzer 172, control unit 156 includes a view selector 174 and a filter stage 176. View selector 174 is operatively connected at an input to analyzer 172 and at an output to video monitor 158 for selecting an image for display from among a multiplicity of possible images of the internal organs detected by analyzer 172. View selector 174 may be provided with an input 178 from a keyboard (not shown) or other operator interface device for enabling an operator to select a desired view. For example, during the insertion of a medical diagnostic or treatment instrument into the patient or during manipulation of that instrument to effect an operation on a targeted internal organ of the patient, the medical practitioner may sequentially select views from different angles to optimize the practitioner's perception of the spatial relation between the distal tip of the instrument and the patient's internal organs.

Filter stage 176 is operatively connected to analyzer 172 and video monitor 158 for optionally eliminating a selected organ from the displayed image. Filter stage 176 is provided with an input 180 from a keyboard (not shown) or other operator interface device for enabling an operator to select an organ for deletion from the displayed image. In one example of the use of filter stage 176, blood moving through a vessel of the vascular system is deleted to enable viewing of the blood vessel walls on monitor 158. This deletion is easily effected starting from conventional techniques such as the Doppler detection of moving bodies.

Filter stage 176 may also function to highlight selected organs. The pattern recognition techniques discussed above are used to detect selected organs. The highlighting may be implemented exemplarily through color, intensity, crosshatching, or outlines.

As further illustrated in FIG. 10, control unit 156 is optionally connected at an output to a frame grabber 182 for selecting a particular image for reproduction in a fixed hard copy via a printer 184. In addition, as discussed hereinabove with respect to the telecommunications links 80a, 80b . . . 80i in FIG. 4, ultrasonically derived real-time image information may be encoded by a modulator 186 onto a carrier wave sent to a remote location via a wireless transmitter 188.

Figure 11:
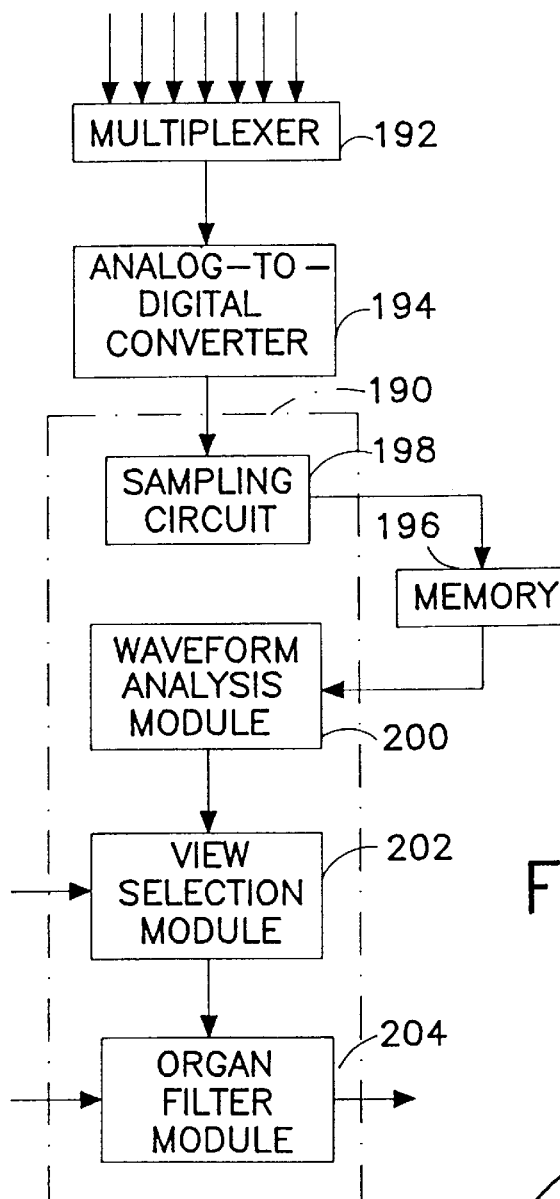
FIG. 11 is a block diagram showing a modification of the apparatus illustrated in FIG. 10.

FIG. 11 depicts the ultrasonography apparatus of FIG. 10 in a form wherein control unit 156 (FIG. 10) is realized as a specially programmed general purpose digital computer 190. A switching circuit or multiplexer 192 relays signals incoming from respective acoustoelectric transducers 168 (FIG. 10) in a predetermined intercalated sequence to an analog-to-digital converter 194, the output of which is stored in a computer memory 196 by a sampling circuit 198 of computer 190. A wave analysis module 200 of computer 190 retrieves the digital data from memory 196 and processes the data to determine three dimensional organic structures inside a patient. This three-dimensional structural data is provided to a view selection module 202 for deriving two-dimensional images for display on monitor 158 (FIG. 10). A filter module 204 is provided for removing selected organs from the image presented on the visual display or video montiro 158. Sampling circuit 198, wave analysis module 200, view selection module 202, and filter module 204 are program-modified generic digital circuits of computer 190.

Figure 12:
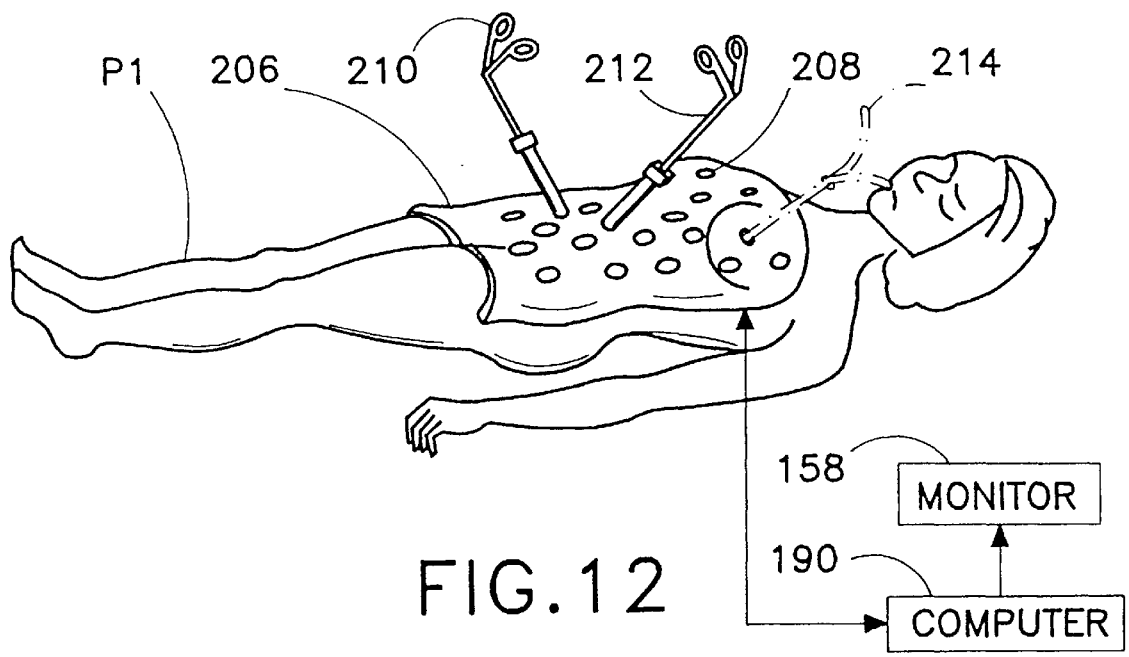
FIG. 12 is partially a schematic perspective view and partially a block diagram showing use of an ultrasonographic imaging device in a minimally invasive diagnostic or therapeutic procedure.

FIG. 12 shows a use of a flexible ultrasonic sensor web 206 which may be any of the flexible ultrasonic sensor webs described herein, except that web 206 is additionally provided with a plurality of apertures or perforations 208. Upon the placement of web 206 in pressure-wave transmitting contact with a skin surface of a patient P, elongate diagnostic or therapeutic instruments such as laparoscopic surgical instruments 210 and 212 are inserted through respective openings 208 to perform a surgical operation on a designated internal organ of the patient P1. This operation is effectuated by viewing a real time image of the distal ends of the instruments 210 and 212 in relation to the patient's internal organic structures as determined by control unit 156 or computer 190. Generally, the image on monitor 158 is viewed during insertion of instruments 210 and 212 to enable a proper employment of those instruments. Also, the video images on monitor 158 are viewed to enable a proper carrying out of the "laparoscopic" surgical operation on the designated internal organ of the patient P1. Strictly peaking, this operation is not a laparoscopic operation, since a laparoscope is not used to provide a continuing image of the patient's internal organic structures and the distal ends of instruments 210 and 212.

There are multiple advantages to using sonographic web 206 instead of a laparoscope. Fewer perforations need be made in the patient for the same number of surgical instruments. In addition, multiple views of the patient's internal organic structures are possible, rather than a single view through a laparoscope. Generally, these multiple views may differ from one another by as little as a few degrees of arc. Also, particularly if web 206 is extended essentially around patient P1, viewing angles may be from under the patient where a laparoscopic could not realistically be inserted.

Web 206 may be used to insert tubular instruments such as catheters and drainage tubes, for example, for thoracentesis and abscess drainage. The tubes or catheters are inserted through apertures 208 under direct real time observation via monitor 158.

In addition to treatment, web 206 may be used to effectuate diagnostic investigations. In particular, a biopsy instrument 214 may be inserted through an aperture 208 to perform a breast biopsy, a liver biopsy, a kidney biopsy, or a pleural biopsy.

Figure 13:
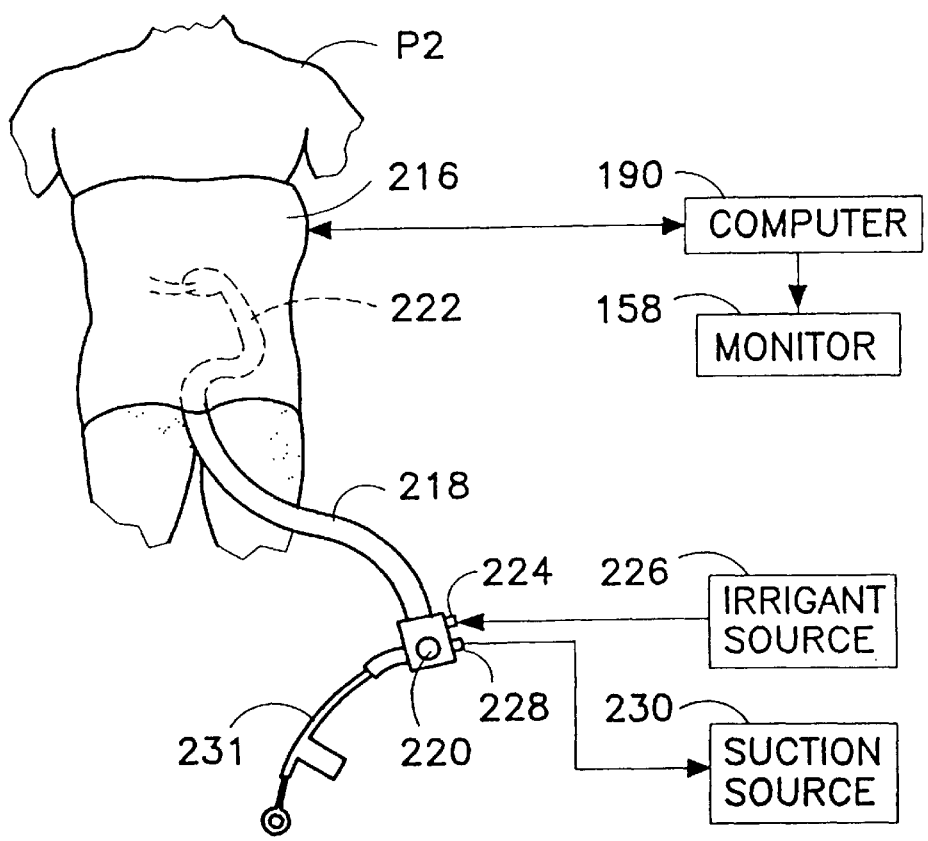
FIG. 13 is a partial schematic perspective view including a block diagram showing use of an ultrasonographic imaging device in another minimally invasive diagnostic or therapeutic procedure.

As illustrated in FIG. 13, a flexible ultrasonic sensor web 216, which may be any of the flexible ultrasonic sensor webs described herein, may be used in a diagnostic or therapeutic operation utilizing a flexible endoscope-like instrument 218. Instrument 218 has a steering control 220 for changing the orientation of a distal tip 222 of the instrument. Instrument 218 also has a port 224 connected to an irrigant source 226 and another port 228 connected to a suction source. In addition, instrument 218 is provided a biopsy channel (not shown) through which an elongate flexible biopsy instrument or surgical instrument 230 is inserted.

Instrument 218 is considerably simplified over a conventional endoscope in that instrument 218 does not require fiber-optic light guides for carrying light energy into a patient P2 and image information out of the patient. Instead, visualization of the internal tissues and organ structures of patient P2 is effectuated via monitor 158 and control unit 156 or computer 190. As discussed above with reference to FIG. 12, the sonographic imaging apparatus if web 216 is extended essentially around patient P2, images may be provided from multiple angles, not merely from the distal tip 222 of instrument 218.

View selector 174 and organ filter stage 176 or view selection module 202 and filter module 204 may function in further ways to facilitate viewing of internal organic structures. In addition to organ removal and highlighting, discussed above, a zoom capability may be provided. The zoom or magnification factor is limited only by the resolution of the imaging, which is determined in part by the frequency of the ultrasonic pressure waves.

Figure 14:
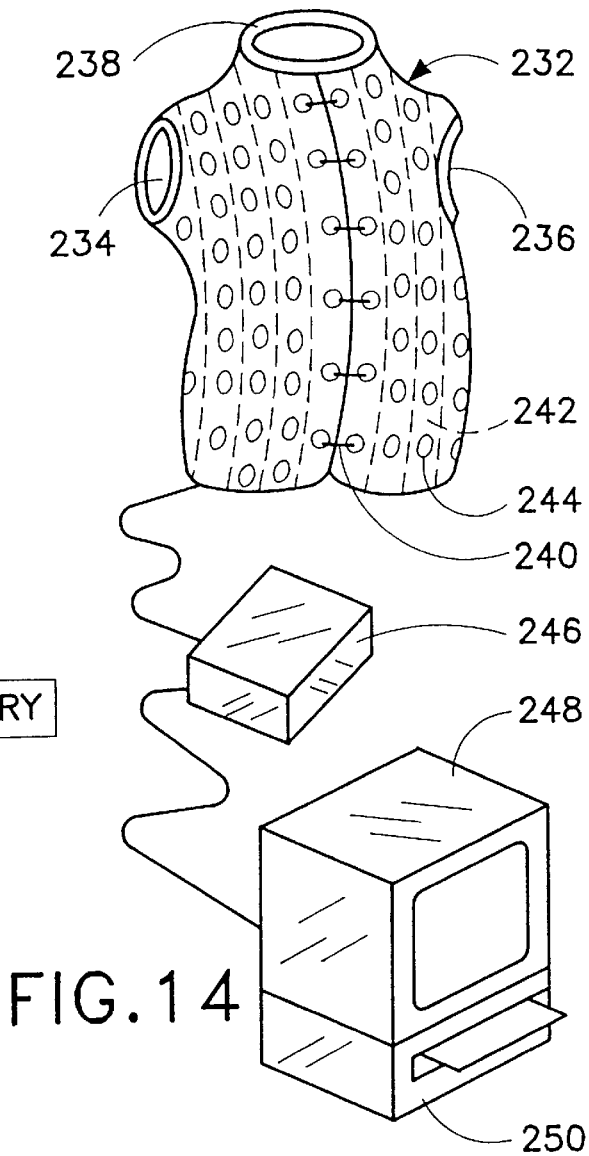
FIG. 14 is a schematic perspective view of yet another ultrasonographic imaging device which includes a sensor vest in a closed, use configuration.
Figure 15:
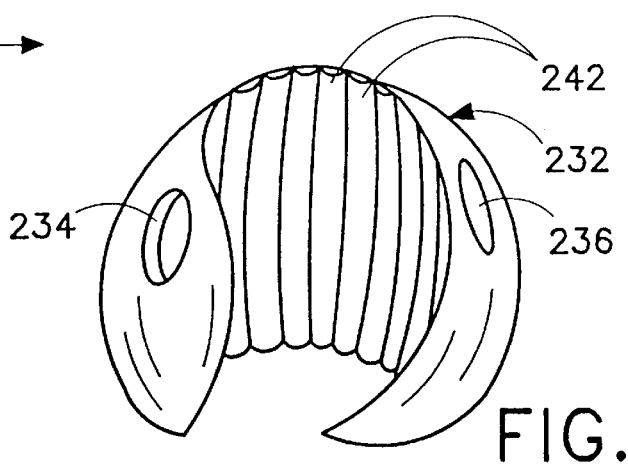
FIG. 15 is a schematic perspective view of the sensor vest of FIG. 14, showing the vest in an open configuration.

FIGS. 14 and 15 depict a specialized ultrasonic sensor web 232 in the form of a garment such as a vest. Sensor vest 232 has arm holes 234 and 236, a neck opening 238 and fasteners 240 for closing the vest about a patient. In addition, sensor vest 232 is provided with a plurality of elongate chambers 242 which receive fluid for expanding the vest into conformation with a patient's skin surface, thereby ensuring contact of the vest with a patient's skin surface and facilitating the transmission of ultrasonic pressure waves to and from ultrasonic transducers 244. FIG. 14 shows a computer 246, a video monitor 248 and a printer 250 used as described above.

Sensor vest 232 may be understood as a container assembly having fluid-filled chambers 242 with flexible inwardly facing walls (not separately designated) which conform to the patient.

Figure 16:
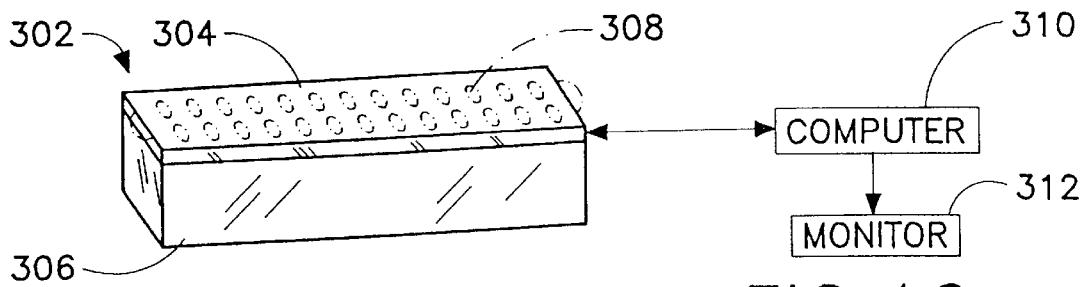
FIG. 16 is partially a schematic perspective view and partially a block diagram of an ultrasonic diagnostic imaging device.
Figure 17:
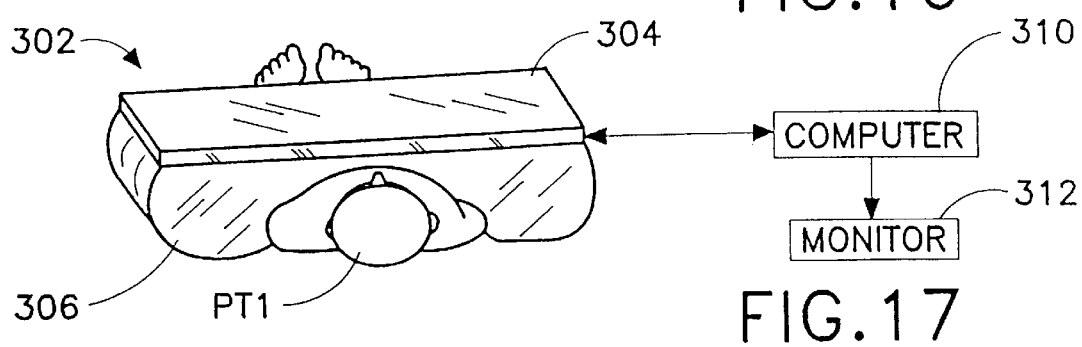
FIG. 17 is partially a schematic perspective view and partially a block diagram of the ultrasonic diagnostic imaging device of FIG. 16, showing the device in use with a patient.

As illustrated in FIG. 16, an ultrasonography apparatus comprises a container assembly 302 including a substantially rigid plate 304 attached to a flexible bladder or bag 306. Bladder or bag 306 is filled with a liquid and is sufficiently flexible to substantially conform to a patient when the container assembly 302 is placed onto a patient PT1, as illustrated in FIG. 17. A liquid may be deposited on the patient prior to the placement of container assembly 302 on patient PT1.

Plate 304 is provided with multiple ultrasonic pressure wave generators and detectors 308 as described above with respect to FIGS. 8 and 9 and FIGS. 14 and 15. Generators and detectors 308 are connected to a computer 310 having essentially the same functional structures and programming as computer 190 for implementing sequential generator energization and sequential detector sampling, as described above. Computer 310 is connected to a monitor 312 for displaying images of internal organs of patient PT1. Computer 310 has the capability of alternately displaying organ images from different angles, as discussed above.

Figure 18:
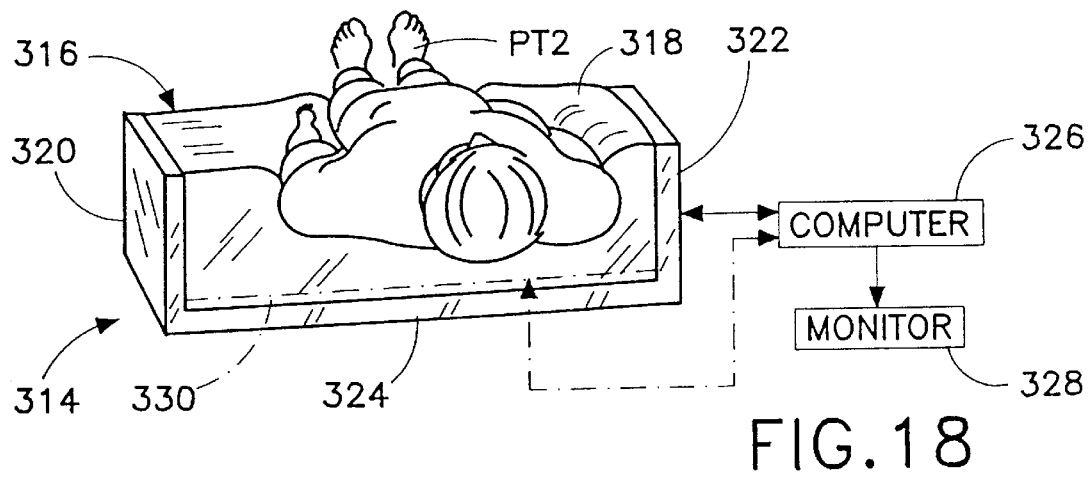
FIG. 18 is partially a schematic perspective view and partially a block diagram of another ultrasonic diagnostic imaging device, showing the device in use with a patient.

FIG. 18 depicts another ultrasonography apparatus useful for both diagnostic investigations and minimally invasive surgical operations. The apparatus comprises a container assembly 314 which includes a fluid-filled sack or bag 316 for receiving a patient PT2. Sack or bag 316 include a flexible upper wall 318 which deforms to conform to the patient PT2 upon placement of the patient onto the bag. Bag 316 is supported on tow or more sides by substantially rigid walls or panels 320 and 322. Panels 320 and 322 are either integral with bag 316 or separable therefrom. Panels 320 and 322, as well as an interconnecting bottom panel 324, may be provided with multiple ultrasonic pressure wave generators and detectors (not shown) as described above with respect to FIGS. 8 and 9, FIGS. 14 and 15, and FIG. 16. These generators and detectors are connected to a computer 326 having essentially the same functional structures and programming as computer 190 for implementing sequential generator energization and sequential detector sampling, as described above. Computer 326 is connected to a monitor 328 for displaying images of internal organs of patient PT2. Computer 326 has the capability of alternately displaying organ images from different angles, as discussed above.

The ultrasonic pressure wave generators and detectors may be provided in a separate carrier 330 disposable, for example, between bottom panel 324 and bag 316, as shown in FIG. 18.

Figure 19:
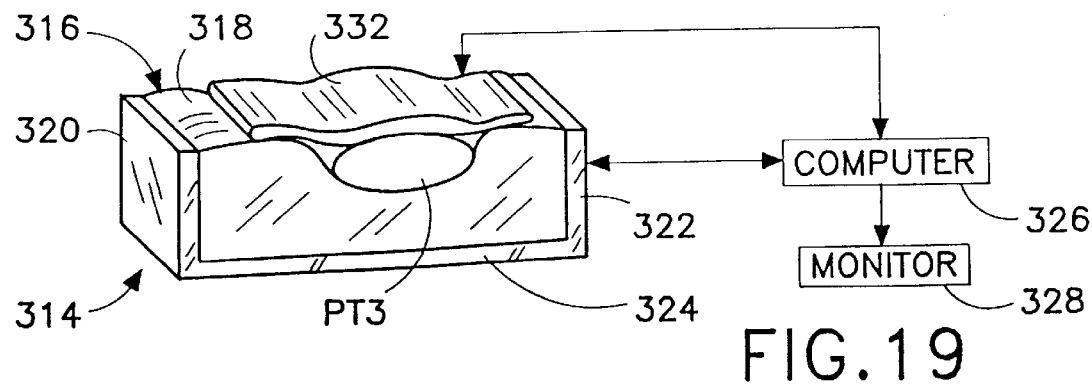
FIG. 19 is partially a schematic perspective view and partially a block diagram of the ultrasonic diagnostic imaging device of FIGS. 17 and 18, showing a modification of the device of those figures.

As illustrated in FIG. 19, the ultrasonography apparatus of FIG. 19 may be used in conjunction with a flexible web or cover sheet 332 identical to web 132, 150, or 206 (FIGS. 8, 9, or 12). Web or cover sheet 332 is operatively connected to computer 326 for providing ultrasonically derived organ position and configuration data to the computer for displaying organ images on monitor 328. The use of web or sheet 332 enables the disposition of ultrasonic wave generators and detectors in a 360° arc about a patient PT3 (diagrammatically illustrated in FIG. 19), thereby facilitating image production. Where web or sheet 332 takes the form of web 206, the sheet is provided with apertures (see FIG. 12 and associated description) for enabling the introduction of minimally invasive surgical instruments into the patient PT3.

As discussed above, contact surfaces are advantageously wetted with liquid to facilitate 20 ultrasonic pressure wave transmission over interfaces.

As discussed hereinafter with reference to FIG. 20, video monitor 158 (FIGS. 10, 12, and 13) or monitor 328 (FIG. 19) may take the form of a flexible video screen layer attached to web 132, 150, 166 or 206 (FIGS. 8, 9, 10, 12) or web 332 (FIG. 19). This modification of the ultrasonographic imaging devices discussed above is considered to be particulary advantageous in medical diagnosis and treatment procedures. The web or subtrate with the video screen is disposed on a selected body portion of a patient, for example, the abdomen (FIGS. 12 and 21) or a shoulder (FIGS. 22A, 22B) or knee (FIG. 23B), so that the substrate and the video screen layer substantially conform to the selected body portion and so that the video screen is facing away from the body portion.

Figure 20:
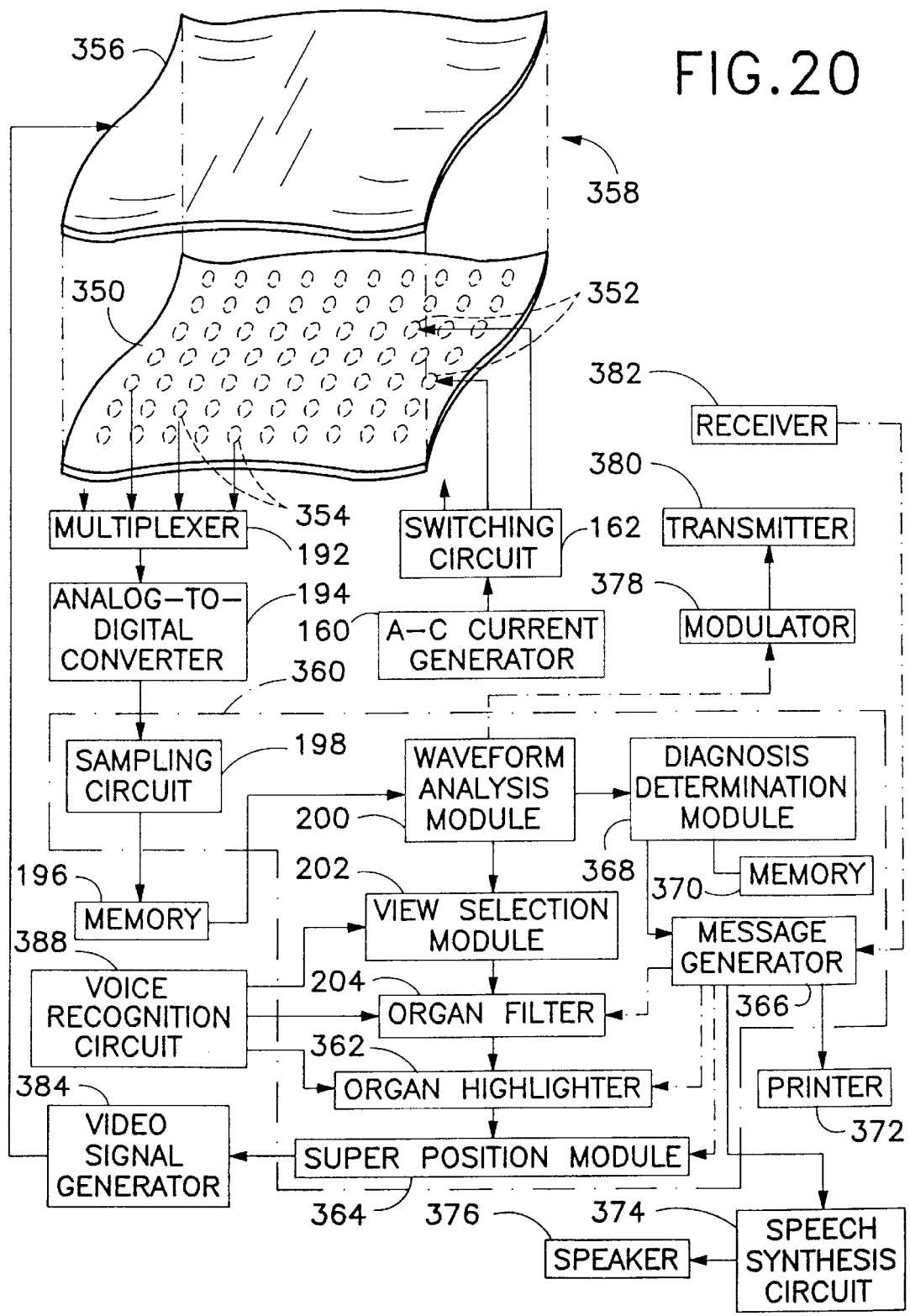
FIG. 20 is partially a schematic exploded perspective view and partially a block diagram of an ultrasonographic device or system related to the present invention.

As shown in FIG. 20, an ultrasonographic device or system comprises a flexible substrate or web 350 which carries a plurality of piezoelectric electroacoustic transducers 352 and a plurality of piezoelectric acoustoelectric transducers 354. A flexible video screen 356 is attached to substrate or web 350 substantially coextensively therewith. Video screen 356 may be implemented by a plurality of laser diodes (not shown) mounted in a planar array to a flexible carrier layer (not separately designated). The diodes are protected by a cover sheet (not separately illustrated) which is connected to the carrier layer. Energization componentry is operatively connected to the diodes for energizing the diodes in accordance with an incoming video signal to reproduce an image embodied in the video signal. In a video monitor, the laser diodes are tuned to different frequency ranges, so as to reproduce the image in color.

The protective cover sheet may function also to disperse light emitted by the laser diodes, to generate a more continuous image.

Substrate or web 350 and video screen 356 comprise an ultrasonic video coverlet or blanket 358 which may be used with the control hardware depicted in FIGS. 10 and 11. Reference numerals used in FIGS. 10 and 11 are repeated in FIG. 20 to designate the same functional components.

Electroacoustic transducers 352 are connected to a-c or ultrasonic signal generator 160 for receiving respective a-c signals of different frequencies. Generator 160 produces different frequencies which are directed to the respective electroacoustic transducers 3 52 by switching circuit 162. Pressure waveforms of different ultrasonic frequencies have different penetration depths and resolutions and provide enhanced amounts of information to a digital signal processor or computer 360. As discussed above with reference to computer 190 of FIG. 11, computer 360 is a specially programmed digital computer wherein functional modules are realized as generic digital processor circuits operating pursuant to preprogrammed instructions.

As discussed above with reference to FIG. 11, switching circuit or multiplexer 192 relays signals incoming from respective acoustoelectric transducers 354 in a predetermined intercalated sequence to analog-to-digital converter 194, the output of which is stored in computer memory 196 by sampling circuit 198. Wave analysis module 200 retrieves the digital data from memory 196 and processes the data to determine three dimensional organic structures inside a patient. This three-dimensional structural data is provided to view selection module 202 for deriving two-dimensional images for display on video screen 256. Filter module 204 serves to remove selected organs, for example, overlying organs, from the image presented on video screen 356. Sampling circuit 198, wave analysis module 200, view selection module 202, and filter module 204 are program-modified generic digital circuits of computer 360.

Computer 360 contains additional functional modules, for example, an organ highlighter 362 and a superposition module 364. The functions of organ highlighter 362 are discussed above with reference to organ filter 176 and 204 in FIGS. 10 and 11. Organ highlighter 362 operates to provide a different color or intensity or cross-hatching to different parts of an image to highlight a selected image feature. For example, a gall bladder or an appendix may be shown with greater contrast than surrounding organs, thereby facilitating perception of the highlighted organ on video screen 356. After organ filter 204 has removed one or more selected organs from an electronic signal representing or encoding an image of internal organs, highlighter 362 operates to highlight one or more features of the encoded image.

Superposition module 364 effects the insertion of words or other symbols on the image displayed on video screen 356. Such words or symbols may, for example, be a diagnosis or alert signal produced by a message generator module 366 of computer 360 in response to a diagnosis automatically performed by a determination module 368 of computer 360. Module 368 receives the processed image information from waveform analysis module 200 and consults an internal memory 370 in a comparison or pattern recognition procedure to determine whether any organ or internal tissue structure of a patient has an abnormal configuration. The detection of such an abnormal configuration may be communicated to the physician by selectively removing organs, by highlighting organs or tissues, or superimposing an alphanumeric message on the displayed image. Accordingly, message generator 366 may be connected to organ filter 204 and organ highlighter 362, as well as to superposition module 364. The communication of an abnormal condition may be alternatively or additionally effectuated by printing a message via a printer 372 or producing an audible message via a speech synthesis circuit 374 and a speaker 376.

As discussed above, the ultrasonically derived three-dimensional structural information from waveform analysis module 200 may be transmitted over a telecommunications link (not shown in FIG. 20) via a modulator 378 and a transmitter 380. The transmitted information may be processed at a remote location, either by a physician or a computer, to generate a diagnosis. This diagnosis may be encoded in an electrical signal and transmitted from the remote location to a receiver 382. Receiver 382 is coupled with message generator module 366, which can communicate the diagnosis or other message as discussed above.

Computer 360 is connected at an output to a video signal generator 384 (which may be incorporated into the computer). Video signal generator 384 inserts horizontal and vertical synchs and transmits the video signal to video screen 356 for displaying an image of internal patient organs thereon.

FIG. 21 diagrammatically depicts a step in a "laparoscopic" cholecystectomy procedure utilizing the ultrasonographic device or system of FIG. 20. Coverlet or blanket 358 is disposed on the abdomen of a patient P2 in pressure-wave transmitting contact with the skin. The skin is advantageously wetted with liquid to facilitate ultrasonic pressure wave transmission. Laparoscopic surgical instruments 210 and 212 (same as in FIG. 12) are inserted through respective openings 386 in coverlet or blanket 358 to perform a surgical operation a gall bladder GB of the patient P2. This operation is effectuated by viewing a real time image of the distal ends of the instruments 210 and 212 in relation to the patient's internal organic structures as determined by computer 360. Generally, the image on video screen 356 is viewed during insertion of instruments 210 and 212 to enable a proper employment of those instruments.

As illustrated in FIG. 21, the gall bladder GB is highlighted (e.g., with greater contrast in screen intensities) relative to other organs such as the liver LV, the stomach ST and the large intestine LI. One or more of these organs may be deleted entirely by organ filter 204. Computer 360 is instructed as to the desired display features via a keyboard (not illustrated in FIG. 20) or a voice recognition circuit 388 operatively connected to various modules 202, 204 and 362. (It is to be noted that speech synthesis circuit 374 and voice recognition circuit 388 enable computer 360 to carry on a conversation with a user. Thus the user may direct the computer to answer questions about the appearance of certain organs selected by the user.)

Generally, the images of the different organs GB, LV, ST and LI, etc., are displayed on video screen 356 so as to substantially overlie the actual organs of the patient P2. To effectuate this alignment of image and organ, markers 390, 392, 394 are placed on the patient P2 at appropriate identifiable locations such as the xyphoid, the umbilicus, the pubis, etc. The markers are of a shape and material which are easily detected by ultrasonic wave analysis and provide computer 360 with a reference frame for enabling the alignment of organ images on screen 356 with the corresponding actual organs. During an operation, view selector 202 may be utilized (via keyboard command or voice recognition circuit 388) to adjust the relative positions of image and organs to facilitate the performance of an invasive surgical operation. As discussed above with reference, for example, to FIG. 13, the ultrasonographic device or system of FIG. 20 may be used in other kinds of procedures.

As illustrated in FIG. 22A, an ultrasonographic coverlet or blanket 396 with attached video screen (not separately designated) and connected computer 398 has a predefined shape conforming to a shoulder SH. The coverlet or blanket 396 is flexible and thus deforms upon motion of the shoulder (FIG. 22B). The coverlet or blanket 396 has a memory so that it returns to the predefined shape when it is removed from the shoulder SH. The flexibility of the coverlet or blanket 396 enables the display in real time of a filtered video image showing the shoulder joint SJ during motion of the shoulder. This facilitates a diagnostic appraisal of the joint.

FIG. 23A illustrates an ultrasonic video cuff 400 with a computer 402. The cuff is attachable in pressure-wave transmitting contact to a knee KN, as depicted in FIG. 23B. Cuff 400 conforms to the knee KN and follows the knee during motion thereof. A knee joint KJ is imaged on the cuff during motion of the knee KN, thereby enabling a physician to study the joint structure and function during motion. Cuff 400 has a memory and returns to its predefined shape (FIG. 23A) after removal from knee KN.

Video screen 356, as well as other video monitors disclosed herein, may be a lenticular lens video display for presenting a stereographic image to a viewer. The ultrasonic processor, e.g., computer 190 or 360, operates to display a three-dimensional image of the internal organs on the lenticular lens video display. 118. Because of the stereoscopic visual input a surgeon is provided via video display 356, he or she is better able to manipulate instruments and 212 during a surgical procedure.

Electroacoustic transducers 134, 164, 352 in an ultrasonographic coverlet or blanket 132, 166, 206, 216, 358 as described herein may be used in a therapeutic mode to dissolve clot in the vascular system. The coverlet or blanket is wrapped around the relevant body part of a patient so that the electroacoustic transducers surround a target vein or artery. First, a scan is effectuated to determine the location of the clot. Then, in a clot dissolution step, the electroacoustic transducers are energized to produce ultrasonic pressure waves of frequencies selected to penetrate to the location of the clot. With a sufficiently large number of transducers transmitting waves to the clot site simultaneously, the clot is disrupted and forced away from the clot site. It is recommended that a filter basket be placed in the pertinent blood vessels downstream of the clot site to prevent any large clot masses from being swept into the brain or the lungs where an embolism would be dangerous.

The monitors disclosed herein, such as monitors 158, 248, 312, 328 and video screen 356, may be provided with a lenticular lens array (not shown) for generating a three-dimensional or stereoscopic display image when provided with a suitable dual video signal. Such a dual signal may be generated by the waveform analysis computer 190, 310, 326, 360 with appropriate programming for the view selection module 202 to select two vantage points spaced by an appropriate distance. Lenticular lens video displays, as well as the operation thereof with input from two cameras, are disclosed in several U.S. patents, including U.S. Pat. No. 4,214,257 to Yamauchi and U.S. Pat. No. 4,164,748 to Nagata, the disclosures of which are hereby incorporated by reference.

It is to be noted that any of the ultrasonography devices or systems disclosed herein may be used in a robotic surgical procedure wherein one or more surgeons are at a remote location relative to the patient. The performance of robotic surgery under the control of the distant experts is disclosed in U.S. Pat. Nos. 5,217,003 and 5,217,453 to Wilk, the disclosures of which are hereby incorporated by reference. Video signals transmitted to the remote location may be generated by the analysis of ultrasonic waves as disclosed herein.

The ultrasonography devices or systems disclosed herein may be used in conjunction with other kinds of scanning devices, for example, spectral diagnosis and treatment devices described in U.S. Pat. Nos. 5,305,748 to Wilk and 5,482,041 to Wilk et al. (those disclosures incorporated by reference herein). It may be possible to incorporate the electromagnetic wave generators and sensors of those spectral diagnosis and treatment devices into the coverlet or blanket of the present invention.

As illustrated in FIG. 24, a medical imaging device comprises a planar firm substrate 404, a substantially flat video screen 406 provided on the substrate, and a flexible bag 408 connected to the substrate. Flexible bag 408 contains a fluidic medium such as water or gel capable of transmitting pressure waves of ultrasonic frequencies and is disposed on a side of the substrate opposite the video screen. As discussed above, a scanner 410 including an ultrasonic waveform generator 412 and a computer-implemented ultrasonic signal processor 414 is operatively connected to video screen 406 for providing a video signal thereto. The video signal encodes an image of internal tissues of a patient PT4 upon placement of medium-containing bag 408, substrate 404, and video screen 406 against the patient. The images of internal tissues and organs off the patient, including the stomach SH, the heart HT, the lungs LG, the small intestine SE, and the large intestine LE, are displayed on screen 406 at positions generally overlying the respective actual tissues and organs of the patient PT4.

Video screen 406 and substrate 404 may be provided with aligned apertures 415 for enabling the traversal of the video screen and the substrate by medical instruments as discussed above with reference to FIG. 21.

Figure 27A:
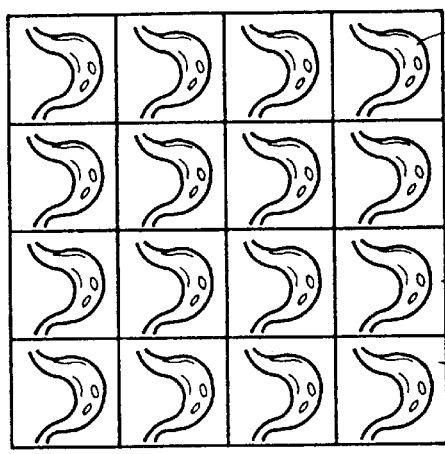
FIG. 27A is a schematic front elevational view of a video screen display configuration utilizable in the ultrasonographic device of FIGS. 25 and 26.

FIGS. 25 and 26 show another medical imaging device comprising a flexible bag 416 containing a fluidic medium such as water or gel. A multiplicity of substantially rigid planar substrates or carrier pads 418 together with respective flat video screens 420 attached thereto are mounted to an upper surface of bag 416. Bag 416 serves in part to movably mount pads 418 with their respective video screens 420 to one another so that the orientations or relative angles of the video screen can be adjusted to conform to a curving surface of a patient PT5, as shown in FIG. 26. Again, a scanner 422 including an ultrasonic waveform generator 424 and a computer-implemented ultrasonic signal processor 426 is operatively connected to video screens 420 for providing respective video signals thereto. The video signals encode respective images of internal tissues of a patient PT5 upon placement of medium-containing bag 416, substrates 418 and video screens 420 against the patient. As illustrated in FIG. 27A, the video images displayed on screen 420 may be substantially the same, with differences in the angle of view of a target organ ORG, depending on the locations and orientations of the respective screens 420. Alternatively, in an enlarged view, a single image of the target organ ORG may be displayed, with each screen 420 displaying only a part of the total image. The technology for implementing these displays over video screens 420 is conventional and well known.

Scanners 410 and 422 are ultrasonic scanners with the same components as other ultrasonic scanners discussed herein, for example, with reference to FIG. 21. Briefly, scanners 410 and 422 each includes a plurality of electroacoustic transducers and a plurality of acoustoelectric transducers disposed in respective arrays along the respective bag 408 or 416 so that ultrasonic pressure waves can travel through the fluidic medium in the respective bag from the electroacoustic transducers and to the acoustoelectric transducers. Computers or processors 414 and 426 analyze incoming digitized ultrasonic sensor signals which are produced in response to ultrasonic pressure waves reflected from various tissue interfaces in the patient PT4 or PT5. From these incoming ultrasonic sensor signals, computers or processors 414 and 426 determine three-dimensional shapes of tissue interfaces and organs inside the patient PT4 or PT5.

As discussed above with reference to FIG. 21, it is recommended that markers be placed in prespecified locations on the patient to enable or facilitate an alignment of the displayed tissue representations and the respective underlying actual tissues. The markers are easily recognized by computer 426 and serve to define a reference frame whereby the positions and the orientations of the multiple video screens 420 relative to the patient's internal tissues are detectable. Thus, the position and the orientation of each video screen 420 relative to the internal tissues and organs of the patient PT5 are determined to enable the display on the video screens 420 of images of selected target tissues of the patient. The reference markers facilitate the display on screens 420 of respective views of the same organ or tissues from different angles depending on the positions and orientations of the various screens 420.

As discussed above, for example, with reference to FIGS. 20 and 21, computers or processor 414 and 426 may include a module 362, typically realized as a programmed general computer circuit, for highlighting a selected feature of the internal organs of patient PT4 or PT5. The highlighting is achievable by modifying the color or intensity of the selected feature relative to the other features in the displayed image, thus providing a visual contrast of the selected feature with respect to the other features of the displayed image. An intensity change may be effectuated by essentially blacking or whiting out the other portions of the image so that the selected feature is the only object displayed on the video screen.

The imaging devices of FIGS. 24 and 26 are optionally provided with a voice-recognition circuit 388 and a speech synthesis circuit 374 (FIG. 20) operatively connected to computer or processor 414 and 426. Advantages and uses of these components are discussed above with reference to FIG. 20. As further described above, computers or processors 414 and 426 are possibly programmed for automated diagnosis based on pattern recognition, with the computed diagnosis being communicated to the user physicians via speech synthesis circuit 374.

Figure 27B:
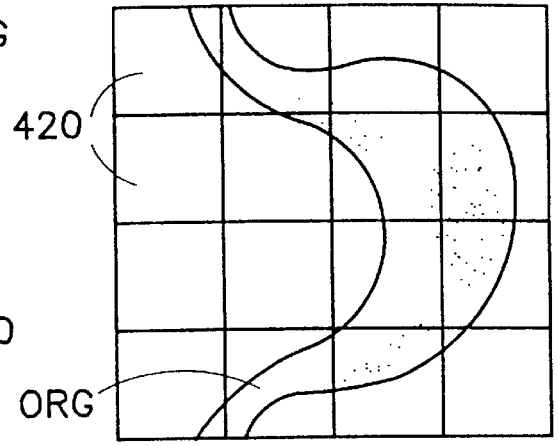
FIG. 27B is a schematic front elevational view of a further video screen display configuration utilizable in the ultrasonographic device of FIGS. 25 and 26.
Figure 28:
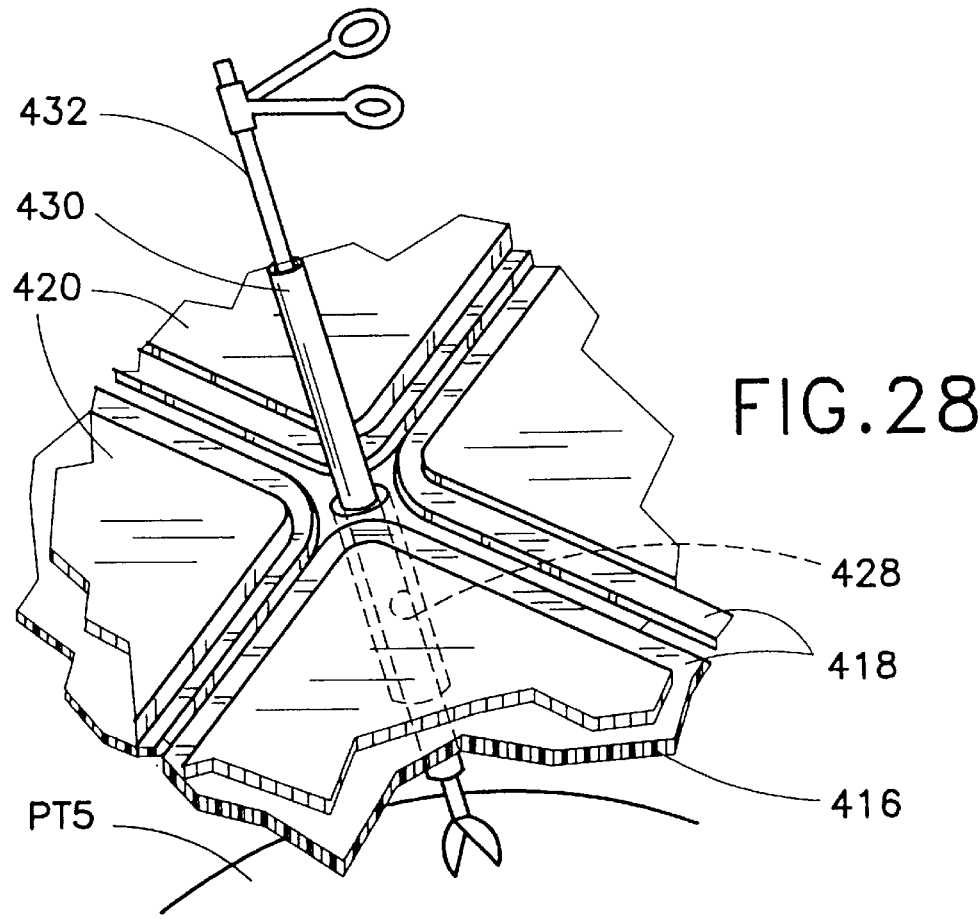
FIG. 28 is a schematic partial perspective view of a modification of the ultrasonographic device of FIGS. 25 and 26, showing a mode of use of the device in a surgical treatement or a diagnostic procedure.

As illustrated in FIG. 28, the imaging device of FIGS. 26 and 27 is advantageously provided with a plurality of apertures or passageways 428 extending through bag 416 in the interstitial spaces between video screens 420. Passageways 428 receive respective tubular cannulas 430 which extend both through the passageways and respective openings (not shown) in the skin and abdominal wall of the patient PT5. Medical instruments such as a laparoscopic forceps 432 are inserted through passageways 428 for performing an operation on internal target tissues of patient PT5 essentially under direct observation as afforded by video screens 420. The distal ends of the medical instruments 432, inserted into patient PT5 in the field of view of the imaging system, are displayed on one or more video screens 420 together with internal target tissues of the patient. The uses of the imaging device of FIGS. 25 and 26 with passageways 428 as illustrated in FIG. 28 are substantially identical to the uses and modes of operation described above with reference to FIGS. 20 and 21.

It is to be noted that bag 416 may be replaced by a plurality of bags (not illustrated) all filled with a fluidic medium through which ultrasonic pressure waves may be transmitted. Each planar substrate or carrier pad 418 and its respective video screen may be attached to a respective fluid-filled bag. In this modification of the ultrasonographic device of FIGS. 25 and 26, apertures performing the function of passageways 428 (FIG. 28) are naturally formed as gaps or spaces between adjacent bags. Separate coupling elements (not illustrated) must be provided between adjacent video screens 420 for forming an integral structure while enabling at least limited flexing between adjacent video screens 420.

It is to be additionally understood that substrates 418 may be formed as carrier layers for active picture elements of video screens 420 and may be visually indistinguishable from the video screens 420.

The imaging devices of FIGS. 24 and 25, 26 may include a transmitter 380 and a receiver 382 (FIG. 20) for operatively connecting scanners 410 and 422 and particularly computers or processors 414 and 426 to a long-distance hard-wired or wireless telecommunications link. As pointed out above, image data transmitted over the telecommunications link to a video monitor at a remote location will enable observation of the patient's internal tissues by distant specialists who may also operate on the patients robotically via the telecommunications link.

Where the imaging device of FIGS. 25–28 is used to diagnose or treat a limb or a joint, planar substrates 418 and video screens 420 have sizes and two-dimensional shapes which facilitate substantial conformity with the limb or joint. To facilitate the use of the imaging device in invasive surgical procedures, the images provided on video screens 420 may be stereoscopic or holographic. Thus, manipulation of medical instrument 432 so that its distal end engages desired internal tissues is facilitated. The imaging device thus may include elements for providing a stereoscopic or holographic image to a viewer, the scanner including means for energizing the elements to produce the stereoscopic or holographic image.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that multiple images may be provided on a single video screen, pursuant to conventional windows-type overlay techniques. Thus, one window or video image may show an organ from one point of view or angle, while another window on the same screen may show the same organ from a different vantage point. Alternatively, one window may show a first organ, while another window displays one or more organs underlying the first organ. In this case, the underlying organs may be shown in phantom line in the first window, while the overlying organs is shown in phantom lines in the second window. Of course, all such operating modes apply to multiple video screens as well as to a single screen. Thus, one screen may display an overlying organ from one angle, while an adjacent organ displays an underlying organ from a different angle. A display window on a video screen of the present invention may be used alternatively for the display of textual information pertaining to the tissues and organs displayed in other video windows. Such information may include diagnostic information determined by the analyzing computer.

Accordingly, it is to be understood that the drawings and descriptions herein are proferred by way of example to facilitate comprehension of the invention and should not be construed to limit the scope thereof.

What is claimed is:

1. A medical imaging device comprising:
   a plurality of substantially planar substrates;
   at least one flexible connection coupling said substrates to one another so that said substrates are extendable at a variable angle with respect to one another;
   a plurality of video screens, each of said substrates carrying at least one of said video screens; and
   a scanner operatively connected to said video screens for providing respective video signals thereto, said video signals each encoding an image of objects located near a respective one of said substrates.

2. The imaging device defined in claim 1 wherein said scanner is provided with an analyzing component for analyzing scanner sensor signals and determining therefrom three-dimensional shapes of said objects.

3. The imaging device defined in claim 2 wherein said analyzing component includes means for highlighting a selected feature of said objects.

4. The imaging device defined in claim 3 wherein said means for highlighting includes means for varying video image intensity.

5. The imaging device defined in claim 2, further comprising voice-recognition circuitry operatively connected to said analyzing component.

6. The imaging device defined in claim 2, further comprising speech synthesis circuitry operatively connected to said analyzing component.

7. The imaging device defined in claim 2 wherein said analyzing component includes means for performing automated diagnoses based in part on image information derived from said scanner sensor signals.

8. The imaging device defined in claim 2 wherein a plurality of apertures are provided in interstitial spaces between said substrates for enabling traversal of the imaging device by medical instruments.

9. The imaging device defined in claim 2, further comprising a transceiver interface for operatively connecting said scanner, including said analyzing component, to a long-distance telecommunications link.

10. The imaging device defined in claim 2 wherein said scanner includes a view selector operatively connected to said analyzing means and said video screen for selecting said image from among a multiplicity of possible images of said objects.

11. The imaging device defined in claim 2, further comprising a filter stage operatively connected to said analyzing means and said video screen for eliminating a selected object from said image.

12. The imaging device defined in claim 1 wherein said scanner includes at least one electroacoustic transducer, an a-c current generator operatively connected to said transducer for energizing said transducer with an electrical signal of a pre-established ultrasonic frequency to produce a first pressure wave, at least one acoustoelectric transducer, and an analyzing component operatively connected to said acoustoelectric transducer for determining three-dimensional shapes of said objects by analyzing signals generated by said acoustoelectric transducer in response to second pressure waves produced at said objects in response to said first pressure wave.

13. The imaging device defined in claim 12 wherein at least one of the transducers is attached at least indirectly to said substrates.

14. The imaging device defined in claim 13 wherein said scanner includes a flexible bag attached to said substrates and carrying a fluidic medium so that ultrasonic pressure waves can travel through said fluidic medium from said electroacoustic transducer and to said acoustoelectric transducer.

15. The imaging device defined in claim 12 wherein said electroacoustic transducer is one of a plurality of electroacoustic transducers each capable of generating a pressure wave in a respective frequency range different from the frequency ranges of the other of said electroacoustic transducers, said a-c current generator being operatively connected to said electroacoustic transducers for energizing said electroacoustic transducers with electrical signals of different pre-established ultrasonic frequencies to produce respective first pressure waves in the respective frequency ranges, said acoustoelectric transducer being one of a plurality of acoustoelectric transducers capable of sensing pressure waves in a plurality of different frequency ranges.

16. The imaging device defined in claim 1 wherein said video screens include elements for providing a stereoscopic image to a viewer, said scanner including means for energizing said elements to produce said stereoscopic image.

17. The imaging device defined in claim 1 wherein said substrates carry a plurality of electroacoustic transducers attached to said substrates in a predetermined array, said scanner including means for energizing said electroacoustic transducers in a predetermined sequence.

18. The imaging device defined in claim 1 wherein said substrates carry a plurality of acoustoelectric transducers attached to said substrates in a predetermined array, said scanner including means for receiving signals from said acoustoelectric transducers in a predetermined sequence.

19. A medical method comprising:
providing an imaging device including a plurality of planar substrates fastened to one another by at least one flexible connector, each of said substrates carrying a respective video screen, a scanner being operatively connected to said video screens;
disposing said substrates with said video screens on a body portion of a patient so that said substrates and said video screens substantially conform to the body portion of the patient and so that said video screens are facing away from the body portion of the patient; and
after the disposition of said substrates and said video screens on the body portion of the patient, operating said scanner to provide video signals to said video screens, said video signals encoding images of internal tissues of the patient.

20. The method defined in claim 19, further comprising operating said video screens to reproduce said images so that internal tissue representations as displayed on said video screens substantially overlie respective corresponding actual tissues of the patient.

21. The method defined in claim 20, further comprising placing markers on the patient for facilitating the reproducing of said images so that the internal tissue representations on said video screens substantially overlie respective corresponding actual tissues of the patient.

22. The method defined in claim 19 wherein the operating of said scanner to provide said video images includes automatically analyzing scanner sensor signals and determining therefrom three-dimensional shapes of the internal tissues of the patient.

23. The method defined in claim 22, further comprising highlighting a selected feature of the internal tissues of the patient on said video screens.

24. The method defined in claim 19 wherein said imaging device is provided with a plurality of apertures, further comprising:
providing a medical instrument;
inserting a distal end portion of said instrument into the patient through one of said apertures;
after insertion of said distal end portion, manipulating said instrument from outside the patient to perform an operation on at least one of the internal tissues of the patient, said images being viewed on said video screens while said instrument is being manipulated.

25. The method defined in claim 19 wherein said scanner includes at least one electroacoustic transducer, an a-c current generator operatively connected to said transducer, at least one acoustoelectric transducer and an analyzing component operatively connected to said acoustoelectric transducer, the disposing of said substrates with said video screens on the body portion of the patient including placing said substrates in pressure-wave-transmitting contact with the body portion of the patient, the operating of said scanner including:
transmitting a first electrical signal of a pre-established ultrasonic frequency from said current generator to said electroacoustic transducer for energizing said electroacoustic transducer to produce a first pressure wave;
transmitting said first pressure wave into the body portion of the patient;
transmitting, from said acoustoelectric transducer to said analyzing component, a second electrical signal corresponding to a second pressure wave produced at the internal tissues of the patient in response to said first pressure wave; and
operating said analyzing component to determine three-dimensional shapes of the internal tissues of the patient by analyzing said second electrical signal.

26. The method defined in claim 25 wherein said electroacoustic transducer is one of a plurality of electroacoustic transducers and said acoustoelectric transducer is one of a plurality of acoustoelectric transducers, further comprising transmitting a plurality of electrical signals of different pre-established ultrasonic frequencies from said current generator to said electroacoustic transducers for energizing said electroacoustic transducers to produce pressure waves in different ultrasonic frequency ranges, also comprising transmitting, from said acoustoelectric transducers to said analyzing component, electrical signals corresponding to pressure waves produced at the internal tissues of the patient in response to the pressure waves in the different ultrasonic frequency ranges, the operating of said analyzing component to determine three-dimensional shapes of the internal tissues of the patient including analyzing electrical signals from said acoustoelectric transducers.

27. A medical imaging device comprising:
- a planar substrate;
- a substantially flat video screen provided on said substrate;
- a flexible bag connected to said substrate, said bag being disposed on a side of said substrate opposite said video screen, said bag being filled with a fluidic medium capable of transmitting ultrasonic pressure waves; and
- a scanner operatively connected to said video screen for providing a video signal thereto, said video signal encoding an image of internal tissues of a patient upon placement of said flexible bag with said medium, said substrate and said video screen against a patient.

28. The imaging device defined in claim 27 wherein said scanner is an ultrasonic scanner.

29. The imaging device defined in claim 28 wherein said scanner includes at least one electroacoustic transducer and at least one acoustoelectric transducer both attached at least indirectly to said substrate so that ultrasonic pressure waves can travel through said fluidic medium from said electroacoustic transducer and to said acoustoelectric transducer.

30. The imaging device defined in claim 27 wherein said scanner is provided with an analyzing component for analyzing scanner sensor signals and determining therefrom three-dimensional shapes of said objects.

31. The imaging device defined in claim 30 wherein said analyzing component includes means for performing automated diagnoses based in part on image information derived from said scanner sensor signals.

* * * * *